US012648986B2

(12) United States Patent
Izquierdo-Useros et al.

(10) Patent No.: US 12,648,986 B2
(45) **Date of Patent: *Jun. 9, 2026**

(54) PLD FOR USE IN COMBINATION IN THE TREATMENT OF CORONAVIRUS

(71) Applicant: PHARMA MAR, S.A., Madrid (ES)

(72) Inventors: Nuria Izquierdo-Useros, Barcelona (ES); Júlia Vergara-Alert, Barcelona (ES); Pablo Avilés Marín, Madrid (ES); Alejandro Losada González, Madrid (ES); José María Fernández Sousa-Faro, Madrid (ES); Salvador Fudio Muñoz, Madrid (ES)

(73) Assignee: PHARMA MAR, S.A., Madrid (ES)

(*) Notice: Subject to any disclaimer, the term of this patent is extended or adjusted under 35 U.S.C. 154(b) by 750 days.

This patent is subject to a terminal disclaimer.

(21) Appl. No.: 17/908,531

(22) PCT Filed: Mar. 2, 2021

(86) PCT No.: PCT/EP2021/055131

§ 371 (c)(1),
(2) Date: Aug. 31, 2022

(87) PCT Pub. No.: WO2021/175823

PCT Pub. Date: Sep. 10, 2021

(65) Prior Publication Data

US 2023/0158103 A1 May 25, 2023

(30) Foreign Application Priority Data

| | | |
|---|---|---|
| Mar. 2, 2020 | (EP) | 20382152 |
| Mar. 13, 2020 | (EP) | 20382192 |
| Apr. 2, 2020 | (EP) | 20382266 |
| Apr. 27, 2020 | (EP) | 20382339 |
| Sep. 16, 2020 | (EP) | 20382815 |
| Sep. 17, 2020 | (EP) | 20382821 |

(51) Int. Cl.

| | |
|---|---|
| *C07D 307/52* | (2006.01) |
| *A61K 31/138* | (2006.01) |
| *A61K 31/14* | (2006.01) |
| *A61K 31/27* | (2006.01) |
| *A61K 31/341* | (2006.01) |
| *A61K 31/4178* | (2006.01) |
| *A61K 31/435* | (2006.01) |
| *A61K 31/4706* | (2006.01) |
| *A61K 31/472* | (2006.01) |
| *A61K 31/675* | (2006.01) |
| *A61K 31/706* | (2006.01) |
| *A61K 38/05* | (2006.01) |
| *A61K 38/12* | (2006.01) |
| *A61K 38/15* | (2006.01) |
| *A61K 45/06* | (2006.01) |
| *A61P 31/14* | (2006.01) |
| *C07D 403/06* | (2006.01) |
| *C07D 487/04* | (2006.01) |
| *C07D 498/04* | (2006.01) |

(52) U.S. Cl.

CPC .............. *A61K 38/15* (2013.01); *A61K 31/27* (2013.01); *A61K 31/435* (2013.01); *A61K 31/4706* (2013.01); *A61K 31/675* (2013.01); *A61P 31/14* (2018.01)

(58) Field of Classification Search

CPC .. C07D 307/52; C07D 403/06; C07D 487/04; C07D 498/04; A61P 31/14; A61K 31/14; A61K 31/27; A61K 31/138; A61K 31/341; A61K 31/435; A61K 31/472; A61K 31/675; A61K 31/706; A61K 31/4178; A61K 31/4706; A61K 38/05; A61K 38/12; A61K 38/15; A61K 45/06; A61K 2300/00

See application file for complete search history.

(56) References Cited

U.S. PATENT DOCUMENTS

2003/0148933 A1 8/2003 Rinehart et al.
2023/0158102 A1* 5/2023 Fernández Sousa-Faro ................ A61P 31/14 514/1.5
2023/0295236 A1* 9/2023 Avilés Marín ..... A61K 31/4178 514/1.4

FOREIGN PATENT DOCUMENTS

WO 199104985 4/1991

OTHER PUBLICATIONS

Cavalcanti, et al. "Hydroxychloroquine with or without Azithromycin in Mild-to-Moderate Covid-19". N. Engl. J. Med. NEJMoa2019014, Jul. 23, 2020.
Elfiky, A.A. "Ribavirin, Remdesivir, Sofosbuvir, Galidesivir, and Tenofovir against SARS-CoV-2 RNA dependent RNA polymerase (RdRp): A molecular docking study", Life Sci. 253, 117592, Mar. 25, 2020.
Hadjadj,et al. "Impaired type I interferon activity and inflammatory responses in severe COVID-19 patients". Science eabc6027, Aug. 7, 2020.
Haviernik, et al. "Arbidol (Umifenovir): A Broad-Spectrum Antiviral Drug That Inhibits Medically Important Arthropod-Borne Flaviviruses". Viruses 10, 184, Apr. 10, 2018.
Jeon, et al. "Identification of antiviral drug candidates against SARS-CoV-2 from FDA-approved drugs", Antimicrobial Agents and Chemotherapy, vol. 64, Issue 7, Jun. 23, 2020.

(Continued)

*Primary Examiner* — Brenda L Coleman
(74) *Attorney, Agent, or Firm* — Ballard Spahr LLP

(57) ABSTRACT

The use of PLD with one or more further CoV antiviral agent(s) in the treatment of coronavirus (CoV) infection.

26 Claims, 5 Drawing Sheets

(56) References Cited

OTHER PUBLICATIONS

Li. "An exploratory randomized controlled study on the efficacy and safety of lopinavir/ritonavir or arbidol treating adult patients hospitalized with mild/moderate COVID-19 (ELACOI)". MedRxiv 33, Apr. 15, 2020.
Lu, et al. "Lipid rafts are involved in SARS-CoV entry into Vero E6 cells". Biochem. Biophys. Res. Commun. 369, 344-349, Feb. 3, 2008.
Maisonnasse, et al. "Hydroxychloroquine use against SARS-CoV-2 infection in non-human primates", Nature, vol. 585, Sep. 24, 2020.
Richardson, et al. "Baricitinib as potential treatment for 2019-nCoV acute respiratory disease". The Lancet 395, e30-e31, Feb. 15, 2020.
Schneider, et al. "Severe Acute Respiratory Syndrome Coronavirus Replication Is Severely Impaired by MG132 due to Proteasome-Independent Inhibition of M-Calpain", J. Virol. 86, 10112-10122, Jul. 11, 2012.
Stebbing, et al. "COVID-19: combining antiviral and anti-inflammatory treatments". Lancet Infect. Dis. 20, 400-402, Feb. 27, 2020.
Tu, et al. "A Review of SARS-CoV-2 and the Ongoing Clinical Trials". Int. J. Mol. Sci. 21, 2657, Apr. 10, 2020.
Wang, et al. "Remdesivir in adults with severe COVID-19: a randomised, double -blind, placebo-controlled, multicentre trial", The Lancet SO 140673620310229, May 16, 2020.
Williamson, et al. "Clinical benefit of remdesivir in rhesus macaques infected with SARS-CoV-2", Nature, 585(7824):273-276, Sep. 10, 2020.
Wu, et al. "Analysis of therapeutic targets for SARS-CoV-2 and discovery of potential drugs by computational methods" Acta Pharm. Sin. B 10 (5), 766-788, May 1, 2020.
Zhou and Simmons, "Development of novel entry inhibitors targeting emerging viruses", Expert Rev. Anti Infect. Ther. 10 (10), 1129-1138, Oct. 1, 2012.
World-First Approval for Multiple Myeloma Drug Aplidin®, Specialised Therapeutics Asia, Dec. 11, 2018.
De Savi, et al., "Quest for a COVID-19 Cure by Repurposing Small-Molecule Drugs: Mechanism of Action, Clinical Development, Synthesis at Scale, and Outlook for Supply", Organic Process Research & Development, 2020, vol. 24, pp. 940-976, available online Jun. 2, 2020.
Losada, et al. Generation of endoplasmic reticulum stress and inhibition of autophagy by plitidepsin induces proteotoxic apoptosis in cancer cells, Biochem Pharmacol. 172:113744, Feb. 1, 2020.
Clinical Trial information—APL-D-002-20 Multicenter, randomized, parallel and proof of concept study to evaluate the safety profile of three doses of Plitidepsin in patients with COVID-19 requiring hospitalization. Mar. 22, 2021.
Harrison, "Drug researchers pursue new lines of attack against COVID-19", Nature Biotechnology, vol. 38, 655-664, Jun. 2020.
Bronstrup and Sasse. Natural products targeting the elongation phase of eukaryotic protein biosynthesis. Nat. Prod. Rep., 37, 752, Jun. 2020.
Cavasotto and Di Filippo, "In silico Drug Repurposing for COVID-19 Targeting SARS CoV-2 Proteins through Docking and Consensus Ranking" Mol. inf. 40, 2000115, first published Jul. 28, 2020.
White et al. "Repurposing of clinically-approved drugs for the treatment of COVID-19", Report from the isirv-AVG Virtual Conference, Oct. 6-8, 2020.
Rodon et al. "Preclinical search of SARS-CoV-2 inhibitors and their combinations within approved drugs to tackle COVID-19 pandemic", doi: https://doi.org/10.1101/2020.04.23.055756, posted Oct. 20, 2020.
Plitidepsin could fight COVID-19., CEN.ACS.org, Feb. 1, 2021.
Gassen, et al. "Analysis of SARS-CoV-2-controlled autophagy reveals spermidine, MK-2206, and niclosamide as putative antiviral therapeutics", Microbiology, posted Apr. 15, 2020.
Hoffmann, et al. "The novel coronavirus 2019 (2019-nCoV) uses the SARS-coronavirus receptor ACE2 and the cellular protease TMPRSS2 for entry into target cells", Molecular Biology, posted Jan. 31, 2020.
Langmead and Salzberg, "Fast gapped-read alignment with Bowtie 2", Nature Methods, vol. 9, No. 4, Apr. 2012.
Corman et al. "Detection of 2019 novel coronavirus (2019-nCoV) by real-time RT-PCR". Euro Surveill.; 25(3): pii=2000045, Jan. 23, 2020.
Marcel Martin. Cutadapt removes adapter sequences from high-throughput sequencing reads EMBnet.journal 17(1), May 2011.
Li et al. The Sequence Alignment/Map format and SAMtools, Bioinformatics—vol. 25 No. 16, pp. 2078-2079, Jun. 8, 2009.
Anonymous, "PharmaMar anuncia resultados positivos de Aplidin contra el coronavirus HCoV-229E", Mar. 13, 2020.
Anonymous, "Boryung Pharmaceutical, PharmaMar's partner in South Korea, announces superior potent results for plitidepsin (Aplidin ) against SARS-CoV-2", Jul. 2, 2020.
Hyun-Tai Shim, "Boryung finds cancer drug has antiviral effect on Covid-19" Korea Biomedical Review, Jul. 2, 2020.
Anonymous, "PharmaMar has announced that the Spanish Medicines Agency has authorized the APLICOV-PC clinical trial with Aplidin (plitidepsin) for the treatment of paients with COVID-19", Apr. 28, 2020.
Anonymous, "History of Changes for Study: NCT04382066—Proof of Concept Study to Evaluate the Safety Profile of Plitidepsin in Patients with COVID-19 (APLICOV-PC)", May 8, 2020.
White et al., "Plitidepsin has potent preclinical efficacy against SARS-CoV-2 by targeting the host protein eEF1A", Science 371, pp. 926-931, Feb. 26, 2021.
Anonymous, "Proof of Concept study to evaluate the safety profile of plitidepsin in patients with COVID-19", Dec. 23, 2020.
Beigel, et al., "Remdesivir for the Treatment of Covid-19—Preliminary Report", New England Journal of Medicine 383; 10, Sep. 3, 2020.
Anonymous, "History Changes for Study: NCT04334460", Last Update Posted Apr. 6, 2020, printed Apr. 5, 2021.
Riva, et al., "Discovery of SARS-CoV-2 antiviral drugs through large-scale compound repurposing", Nature, vol. 586, Jul. 24, 2020.
Li et al., "Is hydroxychloroquine beneficial for COVID-19 patients? ", Cell Death and Disease, Jul. 8, 2020.
Liu et al., "Cathepsin L-selective inhibitors: A potentially promising treatment for COVID-19 patients", Pharmacology & Therapeutics, vol. 213, May 26, 2020.
Fantini et al., "Structural and molecular modeling studies reveal a new mechanism of action of chloroquine and hydroxychloroquine against SARS-CoV-2 infection", International Journal of Antimicrobial Agents, vol. 55, May 2020.
Elfiky, "Ribavirin, Remdesivir, Sofosbuvir, Galidesivir, and Tenofovir against SARS-CoV-2 RNA dependent RNA polymerase (RdRp): A molecular docking study", Life Sciences, vol. 253, Mar. 25, 2020.
Wang, et al., "Remdesivir and chloroquine effectively inhibit the recently emerged novel coronavirus (2019-nCoV) in vitro", Cell Research, Feb. 4, 2020.
PharmaMar reports positive results for Aplidin® against coronavirus HCoV-229E. Pharmamar Press Release (see https://pharmamar.com/en/company/newsroom/), Mar. 13, 2020.
Communication to National Securities Market Commission (Registration No. 82) Pharmamar Press Release (see https://www.cnmv.es/Portal/verDoc.axd?t={bfcd6a1c-d209-42a6-8096-7a953198f8a1}), Mar. 3, 2020.
Communication to National Securities Market Commission (Registration No. 90) Pharmamar Press Release (see https://www.cnmv.es/Portal/verDoc.axd?t={67a1abfd-9477-4f3a-b030-ff7f5b2d958a}), Mar. 13, 2020.
PharmaMar has submitted a Phase II clinical trial of Aplidin® (plitidepsin) for the treatment of COVID-19 to the Spanish Medicines Agency . Pharmamar Press Release (see https://pharmamar.com/en/company/newsroom/), Apr. 2, 2020.
Boryung Pharmaceutical, PharmaMar's partner in South Korea, announces superior potent results for plitidepsin (Aplidin®) against SARS-CoV-2. Pharmamar Press Release (see https://pharmamar.com/en/company/newsroom/), Jul. 2, 2020.

(56) References Cited

OTHER PUBLICATIONS

PharmaMar has announced that the Spanish Medicines Agency has authorized the APLICOV-PC clinical trial with Aplidin® (plitidepsin) for the treatment of patients with COVID-19 . Pharmamar Press Release (see https://pharmamar.com/en/company/newsroom/), Apr. 28, 2020.
Communication to National Securities Market Commission (Registration No. 188)Pharmamar Press Release (see https://www.cnmv.es/Portal/verDoc.axd?t={45a5606c-8cf9-420f-9ef1-5792f3cf697c}), Apr. 28, 2020.
Clinical Trials Study: NCT04382066. Proof of Concept Study to Evaluate the Safety Profile of Plitidepsin in Patients With COVID-19 (APLICOV-PC) https://clinicaltrials.gov/ct2/show/NCT04382066, May 11, 2020.
Luesch, et al. Targeting and extending the eukaryotic druggable genome with natural products. Natural Product Reports, 37(6), 744-746, May 11, 2020.
Rodon et al. Search for SARS-CoV-2 inhibitors in currently approved drugs to tackle COVID-19 pandemia, Apr. 24, 2020.
Korean Biomedical Review report of Boryung data. "Boryung finds cancer drug has antiviral effect on Covid-19", http://www.koreabiomed.com/news/articleView.html?idxno=8662, Jul. 2, 2020.
Press Release by Boryung Pharmaceutical, "Boryung Pharmaceutical, PharmaMar's partner in South Korea, announces superior potent results for plitidepsin (Aplidin®) against SARS-CoV-2", Jul. 2, 2020.
Agostini, et al. "Coronavirus Susceptibility to the Antiviral Remdesivir (GS-5734) Is Mediated by the Viral Polymerase and the Proofreading Exoribonuclease", mBio, vol. 9, Issue 2, Mar. 6, 2018.
Boryung Pharmaceutical Designates Orphan Drug for Small Cell Lung Cancer New Drug 'Lurbinectedin' https://pharm.boryung.co.kr/publicity/news/view.do?SEQ=4025&list_url=L3B1YmxpY210eS9uZXdzL2xpc3QuZG8/bGlzdFR5cGU9bGlzdCZwYWdlPTE4, Aug. 4, 2020.
El Bairi, et al. "Repurposing anticancer drugs for the management of COVID-19", European Journal of Cancer, vol. 14, pp. 40-61, Sep. 22, 2020.
Al-Horani, et al. Potential Anti-SARS-CoV-2 Therapeutics That Target the Post-Entry Stages of the Viral Life Cycle: A Comprehensive Review. Viruses, vol. 12, No. 10, Sep. 26, 2020.
Derosa, Lisa et al. The immuno-oncological challenge of COVID-19. Nature Cancer, vol. 1, No. 10, pp. 946-964, Oct. 1, 2020.
PharmaMar announces positive results of its APLICOV trial against COVID-19 . Pharmamar Press Release (see https://pharmamar.com/en/company/newsroom/), Oct. 16, 2020.
Communication to National Securities Market Commission (Registration No. 496). Pharmamar Press Release (see https://www.cnmv.es/Portal/verDoc.axd?t={cbc13dcd-9dc3-4ccc-9185-a523a38e7827}), Oct. 16, 2020.
Sultana, et al. Challenges for Drug Repurposing in the COVID-19 Pandemic Era. Frontiers in Pharmacology, vol. 11. arn. 588654, Nov. 6, 2020.
Communication to National Securities Market Commission (Registration No. 565) Pharmamar Press Release (see https://www.cnmv.es/Portal/verDoc.axd?t={3ca9678d-c53d-42a0-afec-e5fce5ccbbf3}), Nov. 10, 2020.
Conte, Marine-Derived Secondary Metabolites as Promising Epigenetic Bio-Compounds for Anticancer Therapy. Therapy. Mar. Drugs 2021, 19, 15. https://doi.org/10.3390/md19010015, Dec. 31, 2020.
Rodon et al. Identification of Plitidepsin as Potent Inhibitor of SARS-CoV-2-Induced Cytopathic Effect after a Drug Repurposing Screen. https://doi.org/10.1101/2020.04.23.055756, Jan. 4, 2021.
White et al. Plitidepsin has potent preclinical efficacy against SARS-CoV-2 by targeting the host protein eEF1A, Science, vol. 371, No. 6532, pp. 926-931, Feb. 26, 2021.
Science Magazine confirms efficacy of PharmaMar's plitidepsin against COVID-19, Pharmamar Press Release (see https://pharmamar.com/en/company/newsroom/), Jan. 26, 2021.
Reuschl et al. Host-directed therapies against early-lineage SARS-CoV-2 retain efficacy against B. 1.1.7 variant. bioRxiv preprint doi: https://doi.org/10.1101/2021.01.24.427991, Feb. 4, 2021.
Martinez. "Plitidepsin: a Repurposed Drug for the Treatment of COVID-19". Antimicrob Agents Chemother 65:e00200-21. https://doi.org/10.1128/AAC.00200-21, Mar. 18, 2021.
Poonam et al. Field-Template, QSAR, Ensemble Molecular Docking, and 3D-RISM Solvation Studies Expose Potential of FDA-Approved Marine Drugs as SARS-CoVID-2 Main Protease Inhibitors. Molecules, 26(4), 936, Feb. 10, 2021.
Taglialatela-Scafati "New hopes for drugs against COVID-19 come from the sea". Marine Drugs, 19(2), 104, Feb. 11, 2021.
UK approves the initiation of the Phase III Neptuno clinical trial with PharmaMar's Aplidin® (plitidepsin) for the treatment of patients with COVID-19. Pharmamar Press Release (see https://pharmamar.com/en/company/newsroom/), Feb. 17, 2021.
Gatti and De Ponti. Drug Repurposing in the COVID-19 Era: Insights from Case Studies Showing Pharmaceutical Peculiarities. Pharmaceutics 2021, 13, 302. https://doi.org/10.3390/pharmaceutics13030302, Feb. 25, 2021.
Wong and Blossom. SARS-CoV-2 dependence on host pathways. Science, 371 (6532), • DOI: 10.1126/science.abg6837, Feb. 26, 2021.
Molina R, et al. Population pharmacokinetics meta-analysis of plitidepsin (Aplidin) in cancer subjects. Cancer Chemother Pharmacology; 64(11):97-108, Oct. 22, 2008.
Boulware, et al. "A Randomized Trial of Hydroxychloroquine as Postexposure Prophylaxis for Covid-19". N. Engl. J. Med. NEJMoa2016638, Jun. 3, 2020.
Caly, et al. "The FDA-approved Drug Ivermectin inhibits the replication of SARS-CoV-2 in vitro". Antiviral Res. 104787, Apr. 3, 2020.
Horby, P., "Dexamethasone in Hospitalized Patients with Covid-19—Preliminary Report", The New England Journal Of Medicine, Jul. 17, 2020.
Drożdżal, S., et al., "FDA approved drugs with pharmacotherapeutic potential for SARS-COV-2 (COVID-19) therapy", Drug Resistance Updates, vol. 53, 100719, Jul. 15, 2020.
Eishabrawy, H.A., SARS-CoV-2: An Update on Potential Antivirals in Light of SARS-CoV Antiviral Drug Discoveries, Vaccines (Basel), vol. 8, No. 2, pp. 335, Jun. 23, 2020.

* cited by examiner

PLD FOR USE IN COMBINATION IN THE TREATMENT OF CORONAVIRUS

FIELD OF THE INVENTION

The present invention relates to the treatment of Coronavirus infection using plitidepsin (PLD) combinations.

BACKGROUND OF THE INVENTION

Coronaviruses (CoVs) are enveloped single-stranded, positive-sense RNA viruses with genomes ranging between 26.2-31.7 kb. This large, capped and polyadenylated genome contains seven common coronavirus genes in the following conserved order: 5'-ORF1a-ORF1b-S-ORF3-E-M-N-3'. ORF1a/b produces a genome-length mRNA (mRNA1) that encodes two overlapping viral replicase proteins in the form of polyproteins 1a (pp1a) and pp1ab. These polyproteins are proteolytically processed by virally encoded proteases into mature nonstructural proteins (nsp1 to nsp16), which assemble to form a membrane-associated viral replicase-transcriptase complex (RTC). The last third of the genome produces subgenomic (sg) mRNAs that encode the four structural proteins, spike (S), envelope (E), membrane (M), and nucleocapsid (N), as well as a number of accessory proteins. CoVs belong to the subfamily Coronavirinae in the family of Coronaviridae of the order Nidovirales. The family includes four genera: α-coronavirus, β-coronavirus, γ-coronavirus and δ-coronavirus. SARS (severe acute respiratory syndrome)-CoV-2 and SARS-CoV are in the β-coronavirus genera and share around 80% of their genomes. The coronavirus N protein is abundantly produced within infected cells. N protein has multiple functions, including binding to viral RNA to form the helical ribonucleocapsid and has a structural role in coronavirus assembly. The N protein has also been proposed to have roles in virus replication, transcription and translation.

Coronaviruses (CoVs) infect a variety of human and animal hosts, causing illnesses that range from gastrointestinal tract infections, encephalitis and demyelination in animals to mostly upper relatively mild respiratory tract infections in humans. However, the zoonotic coronaviruses, SARS-CoV, MERS CoV and SARS-CoV2 can cause severe illness and death. The disease caused by SARS-CoV2 is called Coronavirus disease 2019 or COVID-19.

Plitidepsin (PLD) is a cyclic depsipeptide originally isolated from the marine tunicate *Aplidium albicans*. PLD is also known as Aplidin. PLD is currently undergoing a Proof of Concept Study to Evaluate the Safety Profile of PLD in Patients With COVID-19.

The WHO has declared the 2019-2020 coronavirus outbreak to be a Public Health Emergency of International Concerns (PHEIC). As of 12 Feb. 2021, according to the WHO, there were 107,252,265 cases of SARS-CoV-2 including 2,355,339 deaths. There is no specific treatment for a SARS-CoV infection, including SARS-Cov (which causes SARS) and SARS-CoV-2 (which causes COVID-19). A number of vaccines have been developed and, since December 2020, approved for immunisation of individuals for the prevention of COVID-19. However, due to viral mutation, vaccine take up and/or other factors, there remains high hospitalisation rates for patients having COVID-19.

A large number of agents and varying regimens are being tested on hospitalized patients to determine suitable strategies to manage COVID-19 infection. However, to date, no clear therapeutic strategies have been identified. While some agents have shown efficacy, other have not or have been otherwise unsuitable. As such, there is an urgent un-met medical need for a treatment for CoV infection, and in particular a treatment for COVID-19. The present invention addresses this need.

SUMMARY OF THE INVENTION

In one aspect, the present invention is directed to PLD or a pharmaceutically acceptable salt or stereoisomer thereof, for use in the treatment of coronavirus (CoV) infection, wherein PLD or a pharmaceutically acceptable salt or stereoisomer thereof is used in combination with one or more further CoV antiviral agent(s).

It has been surprisingly found that combinations according to the present invention retain activity and do so with acceptable toxicity.

In a further aspect there is provided one or more further CoV antiviral agent(s), for use in the treatment of coronavirus (CoV) infection, wherein the one or more further CoV antiviral agent(s) is used in combination with PLD or a pharmaceutically acceptable salt or stereoisomer thereof.

In a further aspect there is provided a method of treating coronavirus (CoV) infection, comprising administering to a patient in need thereof a combination of PLD or a pharmaceutically acceptable salt or stereoisomer thereof, and one or more further CoV antiviral agent(s).

In a further aspect there is provided the use of PLD or a pharmaceutically acceptable salt or stereoisomer thereof, in the manufacture of a medicament for the treatment of coronavirus (CoV) infection, wherein in said treatment one or more further CoV antiviral agent(s) is also administered.

In a further aspect there is provided the use of one or more further CoV antiviral agent(s), in the manufacture of a medicament for the treatment of coronavirus (CoV) infection, wherein in said treatment PLD or a pharmaceutically acceptable salt or stereoisomer thereof is also administered.

In a further aspect there is provided a combination of PLD or a pharmaceutically acceptable salt or stereoisomer thereof, and one or more further CoV antiviral agent(s).

In a further aspect there is provided combination(s) including PLD according to the present invention for use as a medicament.

In a further aspect there is provided combination(s) including PLD according to the present invention for use in the treatment of coronavirus (CoV) infection.

In a further aspect there is provided a pharmaceutical composition comprising a pharmaceutically acceptable diluent and a combination including PLD according to the present invention.

In a further aspect there is provided a kit comprising combination(s) including PLD according to the present invention; said kit optionally further comprising instructions for treating a patient; said instructions optionally providing instructions for the use of combination(s) according to the present invention for use in the treatment of coronavirus (CoV) infection.

Coronavirus (CoV) infection leads to the disease COVID-19. As such:

In a further aspect there is provided PLD or a pharmaceutically acceptable salt or stereoisomer thereof, for use in the treatment of COVID-19, wherein PLD or a pharmaceutically acceptable salt or stereoisomer thereof is used in combination with one or more further CoV antiviral agent(s).

In a further aspect there is provided one or more further CoV antiviral agent(s), for use in the treatment of COVID-19, wherein the one or more further CoV antiviral agent(s)

is used in combination with PLD or a pharmaceutically acceptable salt or stereoisomer thereof.

In a further aspect there is provided a method of treating COVID-19, comprising administering to a patient in need thereof a combination of PLD or a pharmaceutically acceptable salt or stereoisomer thereof, and one or more further CoV antiviral agent(s).

In a further aspect there is provided the use of PLD or a pharmaceutically acceptable salt or stereoisomer thereof, in the manufacture of a medicament for the treatment of COVID-19, wherein in said treatment one or more further CoV antiviral agent(s) is also administered.

In a further aspect there is provided the use of one or more further CoV antiviral agent(s), in the manufacture of a medicament for the treatment of COVID-19, wherein in said treatment PLD or a pharmaceutically acceptable salt or stereoisomer thereof is also administered.

In a further aspect there is provided a combination of PLD or a pharmaceutically acceptable salt or stereoisomer thereof, and one or more further CoV antiviral agent(s).

In a further aspect there is provided combination(s) including PLD according to the present invention for use as a medicament.

In a further aspect there is provided combination(s) including PLD according to the present invention for use in the treatment of COVID-19.

In a further aspect there is provided a pharmaceutical composition comprising a pharmaceutically acceptable diluent and a combination including PLD according to the present invention.

In a further aspect there is provided a kit comprising combination(s) including PLD according to the present invention; said kit optionally further comprising instructions for treating a patient; said instructions optionally providing instructions for the use of combination(s) according to the present invention for use in the treatment of COVID-19.

The following embodiments apply to all aspects of the present invention.

The one or more further CoV antiviral agents may be selected from an agent that inhibits viral entry, inhibits viral-cell fusion, inhibits endocytosis or inhibits viral replication.

The one or more further CoV antiviral agent(s) may be selected from calpain, cathepsin or calpain/cathepsin inhibitors, RNA polymerase inhibitors, clathrin-mediated endocytosis inhibitors, HIV-1 protease inhibitors, serine protease inhibitors, TMPRSS2 inhibitors, IFN stimulated antiviral proteins, PPARα receptor agonists, cholesterol transporter inhibitors, intracellular cholesterol transport inhibitors, ganglioside biosynthesis pathway inhibitors, cholesterol depleting agents, glucocorticoids, agents that inhibits viral fusion with host cell membranes and JAK inhibitors.

The one or more further CoV antiviral agent(s) may be selected from calpain, cathepsin or calpain/cathepsin inhibitors, RNA polymerase inhibitors, clathrin-mediated endocytosis inhibitors, HIV-1 protease inhibitors, serine protease inhibitors, TMPRSS2 inhibitors, IFN stimulated antiviral proteins and PPARα receptor agonists.

The one or more further CoV antiviral agent(s) may be a cathepsin inhibitor, a cathepsin B inhibitor, a cathepsin L inhibitor, a calpain inhibitor, a combined calpain and cathepsin B inhibitor, a pan cathepsin B/L inhibitor; wherein the agent may preferably be selected from MDL28170, E64d or CA-074; preferably MDL28170.

The one or more further CoV antiviral agent(s) may be an RNA polymerase inhibitor; wherein the agent may preferably be selected from remdesivir or favipiravir; preferably remdesivir.

The one or more further CoV antiviral agent(s) may be a clathrin-mediated endocytosis inhibitor; wherein the agent may preferably be selected from hydroxychloroquine, chloroquine, amantadine or chlorpromazine; preferably hydroxychloroquine or chloroquine; further preferably hydroxychloroquine.

The one or more further CoV antiviral agent(s) may be a HIV-1 protease inhibitor; wherein the agent may preferably be selected from nelfinavir mesylate hydrate, lopinavir, tipranavir, amprenavir or darunavir, preferably nelfinavir mesylate hydrate.

The one or more further CoV antiviral agent(s) may be a serine protease inhibitor, wherein the agent may preferably be selected from camostat, bromhexine, aprotinin or nafamostat, preferably camostat.

The one or more further CoV antiviral agent(s) may be a TMPRSS2 inhibitor; wherein the agent may preferably be selected from camostat, bromhexine, aprotinin or nafamostat, preferably camostat.

The one or more further CoV antiviral agent(s) may be an IFN stimulated antiviral protein; wherein the agent may preferably be selected from interferon 2 alfa or interferon gamma.

The one or more further CoV antiviral agent(s) may be a PPARα receptor agonist; wherein the agent may preferably be fenofibrate.

The one or more further CoV antiviral agent(s) may be inhibit a cholesterol transporter to inhibit intracellular cholesterol transport; wherein the agent may preferably be itraconazole.

The one or more further CoV antiviral agent(s) may be a ganglioside biosynthesis pathway inhibitor; wherein the agent may preferably be NB-DNJ.

The one or more further CoV antiviral agent(s) may be a cholesterol depleting agent; wherein the agent may preferably be methyl-beta cyclodextrin.

The one or more further CoV antiviral agent(s) may be a glucocorticoid; wherein the agent may preferably be ciclesonide.

The one or more further CoV antiviral agent(s) may be an agent that inhibits viral fusion with host cell membranes; wherein the agent may preferably be arbidol.

The one or more further CoV antiviral agent(s) may be a JAK inhibitor; wherein the agent may preferably be tofacitinib.

PLD or a pharmaceutically acceptable salt or stereoisomer thereof and the one or more further CoV antiviral agent(s) may be administered concurrently, sequentially or separately.

The molar ratio of PLD or a pharmaceutically acceptable salt or stereoisomer thereof and the one or more further CoV antiviral agent(s) may be from 1:1000 to 1000:1, 1:700 to 700:1, 1:500 to 500:1, 1:300 to 300:1, 1:100 to 100:1, or 1:50 to 50:1.

The compound may be PLD.

The treatment of coronavirus (CoV) infection may be use in reducing complications associated with CoV infection, including hospitalization, ICU and death.

The treatment of coronavirus (CoV) infection may be use in the prophylaxis, reduction or treatment of COVID persistent (also known as long COVID or post-COVID syndrome).

The treatment of coronavirus (CoV) infection may be use in the treatment of pneumonia caused by COVID-19.

The treatment of coronavirus (CoV) infection may be use in reducing the infectivity of CoV patients. The patients may be asymptomatic or not very symptomatic patients.

The treatment of coronavirus (CoV) infection may be use in reducing the occurrence of supercontagators (asymptomatic or not very symptomatic patients with high viral loads (e.g. TC<25)).

In addition to PLD or a pharmaceutically acceptable salt or stereoisomer thereof and one or more further CoV antiviral agent(s), the combinations of the present invention may further comprise a corticosteroid. In these embodiments, the regimen would comprise PLD or a pharmaceutically acceptable salt or stereoisomer thereof, one or more further CoV antiviral agent(s), and a corticosteroid. The corticosteroid may be administered concurrently, separately or sequentially to the combinations of the present invention. The corticosteroid may be dexamethasone.

The CoV infection may be mild infection; and/or moderate infection; and/or severe infection.

The CoV infection may be acute CoV infection, preferably wherein the CoV infection is acute COVID-19 infection; and/or may be ongoing symptomatic CoV infection, preferably wherein the CoV infection is ongoing symptomatic COVID-19 infection; and/or may be post-CoV syndrome, CoV persistent or long CoV; preferably wherein the CoV infection is post-COVID-19 syndrome, COVID persistent or long COVID. The post-CoV syndrome, CoV persistent or long CoV may include one or more symptoms arising from the cardiovascular, respiratory, gastrointestinal, neurological, musculoskeletal, metabolic, renal, dermatological, otolaryngological, haematological and autonomic systems; psychiatric problems, generalised pain, fatigue and/or persisting fever.

The use may be in the treatment of a patient with signs and symptoms of CoV infection (preferably COVID-19) for up to 4 weeks; and/or from 4 weeks to 12 weeks; and/or for more than 12 weeks.

The use may be in the prophylaxis, reduction or treatment of COVID persistent, long COVID or post-COVID syndrome; preferably wherein the prophylaxis, reduction or treatment minimises the likelihood that a patient suffers from COVID persistent, long COVID or post-COVID syndrome symptoms; and/or reduces the severity of such symptoms; further preferably wherein the treatment minimising the symptoms of CoV infection.

The treatment may reduce the infectivity of CoV patients; including wherein the patient is asymptomatic or not very symptomatic yet has a high viral load.

PLD or a pharmaceutically acceptable salt or stereoisomer thereof may be administered according to a regimen of a once daily dose for 10 days, 9 days, 8 days, 7 days, 6 days, 5 days, 4 days, 3 days, 2 days or 1 day; preferably 2-5 days, 3-5 days, or 3, 4 or 5 days; most preferably 3 days or 5 days; most preferably 3 days.

PLD or a pharmaceutically acceptable salt or stereoisomer thereof may be administered at a dose of 5 mg a day or less, 4.5 mg a day or less, 4 mg a day or less, 3.5 mg a day or less, 3 mg a day or less, 2.5 mg a day or less or 2 mg a day or less; 0.5 mg/day, 1 mg/day, 1.5 mg/day, 2 mg/day, 2.5 mg/day, 3 mg/day, 3.5 mg/day, 4 mg/day, 4.5 mg/day, or 5 mg/day; preferably 1 mg/day, 1.5 mg/day, 2 mg/day or 2.5 mg/day; preferably 1.5-2.5 mg/day; further preferably 1.5 mg/day, 2 mg/day or 2.5 mg/day.

PLD or a pharmaceutically acceptable salt or stereoisomer thereof may be administered at a total dose of 1-50 mg, 1-40 mg, 1-30 mg, 1-20 mg, 1-15 mg, 3-15 mg, 3-12 mg, 4-12 mg, 4-10 mg, or 4.5-10 mg; 4 mg, 4.5 mg, 5 mg, 5.5 mg, 6 mg, 6.5 mg, 7 mg, 7.5 mg, 8 mg, 8.5 mg, 9 mg, 9.5 mg or 10 mg; preferably 4.5 mg, 5 mg, 6 mg, 7.5 mg, 8 mg, 9 mg or 10 mg; more preferably 4.5-7.5 mg/day. The total dose may be split over 1, 2, 3, 4, 5, 6, 7, 8, 9 or 10 days, preferably 3 days or 5 days; most preferably 3 days.

PLD or a pharmaceutically acceptable salt or stereoisomer thereof may be administered at a once daily dose for 3 days at a dose of 1.5-2.5 mg/day. The dose may be 1.5 mg/day. The dose may be 2.5 mg/day.

PLD or a pharmaceutically acceptable salt or stereoisomer thereof may be administered as a 1.5-hour infusion, once a day for 3 consecutive days. 1.5 mg of PLD may be administered as a 1.5-hour infusion, once a day for 3 consecutive days. 2 mg of PLD may be administered as a 1.5-hour infusion, once a day for 3 consecutive days. 2.5 mg of PLD may be administered as a 1.5-hour infusion, once a day for 3 consecutive days. 1 mg of PLD may be administered as a 1.5-hour infusion, once a day for 5 consecutive days. 2 mg of PLD may be administered as a 1.5-hour infusion, once a day for 5 consecutive days.

The regimen may be a single dose (1 day) of PLD or a pharmaceutically acceptable salt or stereoisomer thereof. PLD or a pharmaceutically acceptable salt or stereoisomer thereof may be administered as a single dose of 1-10 mg, 4-10 mg, 4.5-10 mg; 4 mg, 4.5 mg, 5 mg, 5.5 mg, 6 mg, 6.5 mg, 7 mg, 7.5 mg, 8 mg, 8.5 mg, 9 mg, 9.5 mg or 10 mg; preferably 4.5 mg, 5 mg, 6 mg, 7.5 mg, 8 mg, 9 mg or 10 mg; more preferably 5-9 mg, 6.5-8.5 mg, 7-8 mg or 7.5 mg. The compound may be PLD administered as a single dose 1.5-hour infusion.

The single dose regimen may be utilised with all therapies set out in the present invention. The single dose regimen may be utilised with mild infection cases. The single dose regimen may, however, be utilised with moderate and/or severe infection cases. The further addition of corticosteroids (including subsequent corticosteroid administration) may in embodiments be used with the single dose regimen.

The multi-day regimen may be utilised with all therapies set out in the present invention. The multi-day regimen may be utilised with moderate and/or severe infection cases. The multi-day regimen may, however, also be utilised with mild infection cases.

The additional corticosteroid may be administered daily on the same day(s) as administering PLD or a pharmaceutically acceptable salt or stereoisomer thereof. The corticosteroid may be administered on one or more subsequent days. The corticosteroid may be administered on 1, 2, 3, 4, 5, 6, 7, 8, 9, 10 or more subsequent days. The corticosteroid may be administered at a higher dose when administered on the same day as PLD or a pharmaceutically acceptable salt or stereoisomer thereof according to the present invention and at a lower dose on subsequent day(s). The corticosteroid may be dexamethasone.

PLD or a pharmaceutically acceptable salt or stereoisomer thereof may be administered at a dose according to the present invention on days 1-3 of the dosage regimen. The additional corticosteroid may be administered intravenously on days 1-3 of the dosage regimen. The corticosteroid may thereafter be administered by oral administration or IV from Day 4 and up to Day 10 (as per physician judgement according to patient clinical condition and evolution). The corticosteroid may be dexamethasone. The dose may be 6.6 mg/day IV on Days 1 to 3 (for example 8 mg dexamethasone phosphate), followed by dexamethasone 6 mg/day (for example 7.2 mg dexamethasone phosphate or 6 mg dexamethasone base) oral administration or IV from Day 4 and up to Day 10.

In embodiments, dexamethasone is dexamethasone phosphate and is, for example, administered at a dose of 8 mg/day IV on Days 1 to 3, followed by dexamethasone 7.2 mg/day oral administration or IV from Day 4 and up to Day 10.

PLD or a pharmaceutically acceptable salt or stereoisomer thereof may be administered as an infusion, preferably a 1 hour infusion, a 1.5 hour infusion, a 2 hour infusion, a 3 hour infusion or longer; particularly preferably a 1.5 hour infusion.

The regimen may include 1.5 mg of plitidepsin administered as a 1.5-hour infusion, once a day for 3 consecutive days; or 2 mg of plitidepsin administered as a 1.5-hour infusion, once a day for 3 consecutive days; or 2.5 mg of plitidepsin administered as a 1.5-hour infusion, once a day for 3 consecutive days; or 1 mg of plitidepsin administered as a 1.5-hour infusion, once a day for 5 consecutive days; or 2 mg of plitidepsin administered as a 1.5-hour infusion, once a day for 5 consecutive days.

The regimen may include 7.5 mg of plitidepsin administered as a 1.5-hour infusion, as a single dose on day 1.

PLD or a pharmaceutically acceptable salt or stereoisomer thereof may be administered using a loading dose and a maintenance dose.

The PLD or a pharmaceutically acceptable salt or stereoisomer thereof component of the regimen according to the present invention may be:

- a loading dose of 2.5 mg for day 1, and followed by a maintenance dose of 2 mg/day for subsequent days;
- a loading dose of 2.5 mg for day 1, and followed by a maintenance dose of 1.5 mg/day for subsequent days;
- a loading dose of 2.5 mg for day 1, and followed by a maintenance dose of 1 mg/day for subsequent days;
- a loading dose of 2.5 mg for day 1, and followed by a maintenance dose of 0.5 mg/day for subsequent days;
- a loading dose of 2 mg for day 1, and followed by a maintenance dose of 1.5 mg/day for subsequent days;
- a loading dose of 2 mg for day 1, and followed by a maintenance dose of 1 mg/day for subsequent days;
- a loading dose of 2 mg for day 1, and followed by a maintenance dose of 0.5 mg/day for subsequent days;
- a loading dose of 1.5 mg for day 1, and followed by a maintenance dose of 1 mg/day for subsequent days;
- a loading dose of 1.5 mg for day 1, and followed by a maintenance dose of 0.5 mg/day for subsequent days; or
- a loading dose of 1 mg for day 1, and followed by a maintenance dose of 0.5 mg/day for subsequent days.

PLD or a pharmaceutically acceptable salt or stereoisomer thereof may be administered in combination with an additional corticosteroid. The corticosteroid may be administered on the same days as administration of PLD.

The corticosteroid may also be administered on one or more subsequent days; for example wherein the corticosteroid is administered with PLD on days 1-3 and the corticosteroid is further administered on one or more of days 4-10.

The corticosteroid may be administered intravenously on days when PLD is administered but administered by oral administration or IV on subsequent days.

The corticosteroid may be dexamethasone. Dexamethasone may be administered at a dose of 6.6 mg/day IV on days when PLD is administered.

Dexamethasone may be administered at a dose of 6 mg/day oral administration or IV on subsequent days, preferably one or more of days 4, 5, 6, 7, 8, 9 and 10.

The dexamethasone dose as defined herein refers to the base weight. The dose can therefore be adjusted if used in salt form. For example, the dexamethasone may be dexamethasone phosphate such that 8 mg/day is equivalent to 6.6 mg of dexamethasone base, and 7.2 mg/day is equivalent to 6 mg of dexamethasone base.

PLD may be administered 1.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution), together with one or more further CoV antiviral agent(s).

PLD may be administered 2.0 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution), together with one or more further CoV antiviral agent(s).

PLD may be administered 2.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution), together with one or more further CoV antiviral agent(s).

The corticosteroid may be administered 20 to 30 minutes prior to starting treatment with PLD.

In regimens according to the present invention, the patient may additionally receive further medications, preferably 20 to 30 minutes prior to starting treatment with PLD or a pharmaceutically acceptable salt or stereoisomer thereof:

- Ondansetron 8 mg IV (or equivalent);
- Diphenhydramine hydrochloride 25 mg IV (or equivalent); and
- Ranitidine 50 mg IV (or equivalent).

In regimens according to the present invention, on Days 4 and 5, patients may receive ondansetron (or equivalent) 4 mg twice a day PO.

When PLD or a pharmaceutically acceptable salt or stereoisomer thereof is administered as a single dose (i.e. on a single day and not part of a multi-day regimen), patients may receive the following prophylactic medications 20-30 minutes prior to plitidepsin infusion:

- Diphenhydramine hydrochloride 25 mg i.v;
- Ranitidine 50 mg i.v;
- Dexamethasone 6.6 mg intravenously;
- Ondansetron 8 mg i.v. in slow infusion of 15 minutes.

Ondansetron 4 mg orally may be given every 12 hours for 3 days after PLD administration to relieve drug-induced nausea and vomiting. If PLD is administered in the morning the patient may receive the first dose of ondansetron in the afternoon.

DESCRIPTION OF THE FIGURES

The invention is further described in the following non-limiting figures.

DETAILED DESCRIPTION

Figure 1:
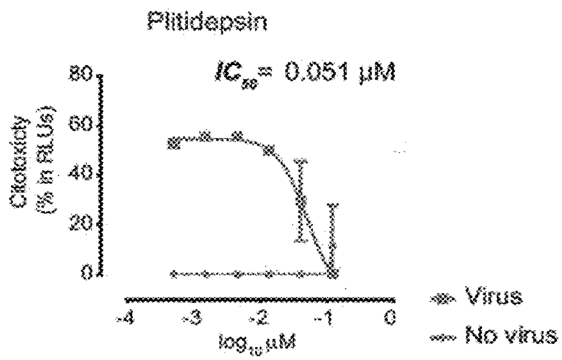
FIG. 1 shows the cytopathic effect on Vero E6 cells exposed to a fixed concentration of SARS-CoV-2 in the presence of increasing concentrations of PLD.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In the present application, a number of general terms and phrases are used, which should be interpreted as follows.

The term "treating", as used herein, unless otherwise indicated, means reversing, attenuating, alleviating or inhibiting the progress of the disease or condition to which such term applies, or one or more symptoms of such disorder or condition. The term treating as used herein may also include prophylactic treatment, that is treatment designed to prevent a disease from occurring or minimize the likelihood of a disease occurring.

"Treat", "treating", and "treatment" may refer to one or more of the following: 1) reduction in the number of infected cells; 2) reduction in the number of virions present in the serum; 3) inhibition (i.e., slowing to some extent, preferably stopping) of rate of CoV replication; and 4) relieving or reducing to some extend one or more of the symptoms associated with CoV infection.

The treatment may be treating CoV infection. The treatment may be treating SARS-CoV-2 infection. The treatment may be treating COVID-19 infection. The treatment may be the treatment of COVID-19. The treatment may be the treatment of a disease that results from infection by CoV. The treatment may be the treatment of a disease that results from infection by SARS-CoV-2. The treatment may be the treatment of pneumonia caused by infection by CoV. The treatment may be the treatment of pneumonia caused by infection by SARS-CoV-2. The treatment may be the treatment of pneumonia caused by infection by COVID-19. The treatment may be the treatment of pneumonia caused by COVID-19.

The infection may be moderate infection. The infection may be severe infection. The infection may be mild infection.

The treatment may be reducing complications associated with CoV infection, including hospitalization, ICU and death.

The present invention may be useful to treat acute COVID-19 infection (signs and symptoms of COVID-19 for up to 4 weeks); treat (or minimise) ongoing symptomatic COVID-19 (signs and symptoms of COVID-19 from 4 weeks up to 12 weeks); or treat or minimise post-COVID-19 syndrome (signs and symptoms that develop during or following an infection consistent with COVID-19, continue for more than 12 weeks and are not explained by an alternative diagnosis. It usually presents with clusters of symptoms, often overlapping, which can fluctuate and change over time and can affect any system in the body. Post-COVID-19 syndrome may be considered before 12 weeks while the possibility of an alternative underlying disease is also being assessed). The compounds of the present invention may treat a patient with signs and symptoms of COVID-19 for up to 4 weeks. The compounds of the present invention may treat a patient with signs and symptoms of COVID-19 from 4 weeks to 12 weeks. The compounds of the present invention may treat a patient with signs and symptoms of COVID-19 for more than 12 weeks.

The treatment may be prophylaxis, reduction or treatment of COVID persistent (also known as long COVID or post-COVID syndrome). The compounds according to the present invention can minimise the likelihood of a patient suffering from COVID persistent symptoms. The compounds according to the present invention may alternatively reduce the severity of such symptoms, preferably may minimise the symptoms of CoV infection.

Post-COVID syndrome may be considered as signs and symptoms that develop during or following an infection consistent with COVID-19 which continue for more than 12 weeks and are not explained by an alternative diagnosis. The condition usually presents with clusters of symptoms, often overlapping, which may change over time and can affect any system within the body. Many people with post-COVID syndrome can also experience generalised pain, fatigue, persisting high temperature and psychiatric problems. Symptoms include (but are not limited to) symptoms arising in the cardiovascular, respiratory, gastrointestinal, neurological, musculoskeletal, metabolic, renal, dermatological, otolaryngological, haematological and autonomic systems, in addition to psychiatric problems, generalised pain, fatigue and persisting fever.

The treatment may be reducing the infectivity of CoV patients. The present invention achieves a rapid and significant reduction in the viral burden. Reducing the viral burden may reduce the infectiveness of patients. This is particular beneficial with patients who are asymptomatic or not very symptomatic patients yet have a high viral loads (e.g. TC<25). Such patients may be supercontagators or superspreaders. Administration of compounds according to the present invention upon detection of infection can reduce the viral burden and therefore reduce the infectiveness of the patient.

The treatment may result in a reduction of viral load. This may be expressed as a replication cycle threshold (Ct) value greater than 30 (Ct>30), on day 6 after the administration. The treatment may reduce viral load from baseline. This may be expressed as a reduction in the percentage of patients requiring hospitalisation following administration. This may be expressed as a reduction in the percentage of patients requiring invasive mechanical ventilation and/or admission to the ICU following administration. This may be expressed as a reduction of patients who develop sequelae related to persistent disease. This may be expressed as an increase in the percentage of patients with normalization of analytical parameters chosen as poor prognosis criteria (including, for example, lymphopenia, LDH, D-dimer or PCR). This may be expressed as an increase in the percentage of patients with normalization of clinical criteria (disappearance of symptoms), including, for example: headache, fever, cough, fatigue, dyspnea (shortness of breath), arthromyalgia or diarrhoea.

"Patient" includes humans, non-human mammals (e.g., dogs, cats, rabbits, cattle, horses, sheep, goats, swine, deer, and the like) and non-mammals (e.g., birds, and the like). The patient may require hospitalisation for management of infection.

PLD (plitidepsin) is a cyclic depsipeptide originally isolated from the marine tunicate *Aplidium albicans*. PLD is also known as Aplidin. In a preferred embodiment, the present invention relates to the use of PLD.

The chemical name of PLD is (−)-(3S,6R,7S,10R,11S,15S,17S,20S,25aS)-11-hydroxy-3-(4-methoxybenzyl)-2,6,17-trimethyl-15-(1-methylethyl)-7-[[(2R)-4-methyl-2-[methyl[[(2S)-1-(2-oxopropanoyl)pyrrolidin-2-yl]carbonyl]amino]pentanoyl]amino]-10-[(1S)-1-methylpropyl]-20-(2-methylpropyl)tetradecahydro-15H-pyrrolo[2,1-f]-[1,15,4,7,10,20]dioxatetrazacyclotricosine-1,4,8,13,16,18,21(17H)-heptaone corresponding to the molecular formula $C_{57}H_{87}N_7O_{15}$. It has a relative molecular mass of 1110.34 g/mol and the following structure:

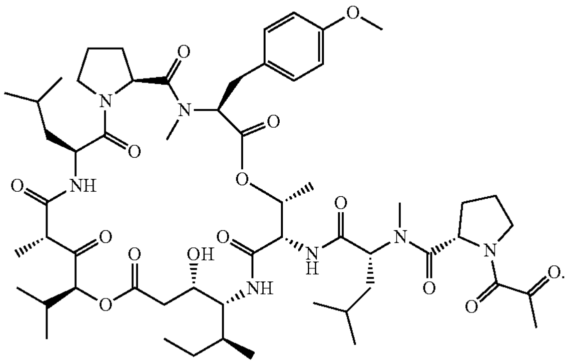 [SMILES: CC[C@H](C)[C@H]1NC(=O)[C@@H](NC(=O)[C@@H](CC(C)C)N(C)C(=O)[C@@H]2CCCN2C(=O)C(C)=O)[C@@H](C)OC(=O)[C@H](Cc2ccc(OC)cc2)N(C)C(=O)[C@@H]2CCCN2C(=O)[C@H](CC(C)C)NC(=O)[C@@H](C)C(=O)[C@H](C(C)C)OC(=O)C[C@@H]1O]

Human translation elongation factor eEF1A, is a subunit of the eukaryotic translation elongation 1 complex (eEF1). This complex delivers aminoacylated tRNA to the elongating ribosomes during protein synthesis. However, eEF1A in not only a major translation factor, but also one of the most important multifunctional proteins, having roles in the quality surveillance of newly synthesised proteins, in ubiquitin-dependent degradation and in facilitating apoptosis.

The N protein of CoVs, such as SARS-CoV and TGEV (transmissible gastroenteritis coronavirus), have been shown to bind directly to eukaryotic elongation factor 1A (eEF1A). Furthermore, knockdown of eEF1A has been shown to lead to a significant reduction in virus number demonstrating that the interaction of the N protein with eEF1A is essential for viral replication.

PLD has been shown to bind to the human translation elongation factor eEF1A with a high-affinity and a low rate of dissociation. FLIM-phasor FRET experiments demonstrate that PLD localises in tumor cells sufficiently close to eEF1A as to suggest the formation of drug-protein complexes in living cells. PLD-resistant cell lines also show reduced levels of eEF1A protein and ectopic expression of eEF1A in these resistant cells restores the sensitivity to PLD, demonstrating that eEF1A is directly involved in the mechanism of action of PLD.

As explained above, the N protein of CoVs also bind to eEF1A, and this binding is essential for viral replication. Furthermore, the N protein is highly conserved within CoVs—and in particular, SARS-CoV-2 shares around 90% amino acid identity with the N-protein in SARS-CoV. However, administration and subsequent binding of PLD to eEF1A prohibits the binding of the CoV N-protein to eEF1A. This in turn prevents virus replication. The interaction between plitidepsin and EF1A could therefore reduce the efficiency of de novo viral capsid synthesis and consequently cause a decrease in viral load.

In addition to the above, PLD binding to eEF1A prevents eEF1A from interacting with its usual binding partners. One such binding-partner is the dsRNA-activated protein kinase (PKR or eIF2AK2). Binding of PLD to eEF1A releases PKR from a complex with eEF1A leading to the activation of PKR. PKR is a known activator of the innate immune response and a key player in anti-viral immune responses. Specifically, (i) activated PKR phosphorylates the alpha subunit of initiation factor eIF2, leading to the formation of an inactive eIF2 complex;

(ii) activated PKR induces the degradation of IκB, nuclear translocation of NF-κB and activation of the NF-κB pathway. NF-κB is a major transcription factor that regulates the genes responsible for both innate and adaptive immune responses, such as genes involved in T-cell development, maturation and proliferation;

(iii) activation of PKR induces apoptosis through a mechanism involving Fas clustering and NF-κB translocation leading to the elimination of infected cells.

Of note, protein 4a of CoVs potently suppresses the activation of PKR through the sequestration of dsRNA. PLD bypasses this viral response, leading to activation of PKR by releasing PKR from the eEF1A complex, as can be seen from the activation of PKR in the absence of viral infection.

Finally—and in addition to the above, binding of PLD to eEF1A also activates the ER-stress induced unfolded protein response (UPR), which in turn leads to a number of anti-viral responses, including again the phosphorylation of eIF2a.

Through a combination of these mechanisms—(i) inhibition of the CoV N-protein/eEF1A interaction; (ii) activation of PKR and (iii) activation of the UPR; PLD prevents CoV replication and causes the activation of host responses that lead to the elimination of CoV. Both of which contribute to an effective viral therapy. An additional advantage of targeting eEF1A is that it is a human target and as such will not mutate to evade PLD the way viral proteins do.

As mentioned above, in eukaryotic cells, FLIM-FRET experiments demonstrated that plitidepsin localises sufficiently close to eEF1A to suggest the formation of drug-protein complexes in the cytoplasm. A separate set of experiments carried out with 14C-plitidepsin and eEF1A purified from rabbit muscle showed that plitidepsin binds eEF1A with high affinity and a low rate of dissociation.

Plitidepsin Activity on SARS-CoV-2 In Vitro

Several in vitro experiments aimed at determining the effect of plitidepsin on SARS-CoV-2 were carried out and are disclosed herein. Two studies, each using Vero E6 cells infected with SARS-CoV-2 and direct quantitation of SARS-CoV-2 nucleocapsid (N) protein, which is clearly involved in the mechanism of plitidepsin-induced antiviral activity, showed that plitidepsin is a potent inhibitor of SARS-CoV-2 growth in vitro, with $IC_{50}$ of 0.7 to 3.0 nM. In another study, human stem cell-derived pneumocyte like cells were prophylactically exposed to 10 nm plitidepsin for 1 hour and then infected with SARS-CoV-2 ($4\times10^4$ plaque forming units). After a 48 hour incubation period, both antiviral and cytotoxic plitidepsin effects were determined. Results showed that plitidepsin completely eliminated replication of SARS-CoV-2 with no observable cytotoxicity against the pneumocyte like cells.

Plitidepsin Effects on SARS-CoV-2 In Vivo

Plitidepsin demonstrated potent antiviral effects in vivo, using a previously described mouse model of adenovirus-mediated hACE2 infected with SARS-CoV-2. Plitidepsin also demonstrated potent antiviral effects in vivo using a previously described model of transgenic mice expressing hACE2 driven by the cytokeratin-18 gene promoter (K18-hACE2) infected with SARS-CoV-2.

Plitidepsin Effects on Host Inflammatory Reaction

Similar to SARS CoV, infection with SARS-CoV-2 also produces hypersecretion of several cytokines, with increasing plasma levels as the disease progresses, suggesting a possible relation between cytokine release and disease severity.

Innate immunity is the first line of defence against invading pathogens. In the case of SARS-CoV-2, the entry of the virus into host epithelial cells is mediated by the interaction between the viral envelope spike (S) protein and the cell surface receptor ACE2. Viral RNAs, as pathogen associated molecular patterns, are then detected by the host pattern recognition receptors, which include the family of toll like receptors. Toll like receptors then upregulate antiviral and proinflammatory mediators, such as interleukin (IL) 6, IL 8, and interferon (IFN)-γ, through activation of the transcription factor nuclear factor kappa B (NF-κB). The importance of NF-κB towards proinflammatory gene expression, particularly in the lungs, has been highlighted by studies exploring SARS CoV infection in nonclinical species as well as in patients. In mice infected with SARS CoV, the pharmacologic inhibition of NF-κB resulted in higher survival rates and reduced expression of tumour necrosis factor alpha (TNFα), CCL2, and CXCL2 in lungs.

Early in vitro studies showed that plitidepsin induces down-regulation of NFκB in tumour cells. Subsequently, both in vitro and ex vivo studies were performed to assess the effects of plitidepsin on immune cells.

In vitro studies were performed using THP-1 cells, a spontaneously immortalised monocyte-like cell line derived from the peripheral blood of a childhood case of acute monocytic leukaemia, that is widely used for investigating monocyte structure and function. Results showed that all the pathogen-associated molecular patterns-mimicking compounds induced the production of proinflammatory cytokines in THP-1 cells and the addition of plitidepsin significantly reduced the secretion of the proinflammatory cytokines.

An ex vivo study assessed the effect of plitidepsin on expression of the cytokines IL 6, IL 10, and TNFα in the lungs of mice. Results showed that cluster of differentiation (CD)45+ cells from placebo treated mice were capable of producing IL 6, IL 10, and TNFα upon LPS-B5 stimulation. However, CD45+ cells from plitidepsin treated mice failed to show a marked increase in IL 6, IL 10, and TNFα compared with nonstimulated controls. These results suggest that the in vivo exposure to plitidepsin prevented the increased production of proinflammatory cytokines mediated by LPS-B5 in the CD45+ cells isolated from bronchoalveolar lavages.

Accordingly, PLD can be used in the treatment of CoV infection.

The term "CoV" infection means any infection from a virus in the family Coronaviridae and the sub-family Orthocoronavirinae. In one embodiment, the infection is from a virus in the genus Betacoronavirus, which includes Betacoronavirus 1, Human coronavirus HKU1, Murine coronavirus, Pipistrellus bat coronavirus HKU5, Rousettus bat coronavirus HKU9, Severe acute respiratory syndrome-related coronavirus (SARS-CoV), Tylonycteris bat coronavirus HKU4, Middle East respiratory syndrome-related coronavirus, Human coronavirus OC43 and Hedgehog coronavirus 1 (EriCoV). Preferably, the virus is SARS-CoV, or SARS-CoV-2, and most preferably SARS-CoV-2. SARS-CoV-2 was previously called 2019-nCoV and such terms may be used interchangeably herein.

In aspects of the invention, the combinations as defined herein may be used in the treatment of COVID-19. COVID-19 is the disease that results from infection by SARS-CoV-2. In aspects of the invention, the combinations as defined herein through their antiviral activity may be used to minimise or prevent the development of COVID-19 associated pneumonia.

The term "pharmaceutically acceptable salts" refers to any salt which, upon administration to the patient is capable of providing (directly or indirectly) a compound as described herein. It will be appreciated that non-pharmaceutically acceptable salts also fall within the scope of the invention since those may be useful in the preparation of pharmaceutically acceptable salts. The preparation of salts can be carried out by methods known in the art. For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic amino acids salts.

The compounds of the invention, including PLD, may be in crystalline form either as free compounds or as solvates (e.g. hydrates, alcoholates, particularly methanolates) and it is intended that both forms are within the scope of the present invention. Methods of solvation are generally known within the art. The compounds of the invention may present different polymorphic forms, and it is intended that the invention encompasses all such forms Any compound referred to herein is intended to represent such specific compound as well as certain variations or forms. In particular, compounds referred to herein may have asymmetric centres and therefore exist in different enantiomeric or diastereomeric forms. Thus any given compound referred to herein is intended to represent any one of a racemate, one or more enantiomeric forms, one or more diastereomeric forms, and mixtures thereof. Likewise, stereoisomerism or geometric isomerism about the double bond is also possible, therefore in some cases the molecule could exist as (E)-isomer or (Z)-isomer (trans and cis isomers). If the molecule contains several double bonds, each double bond will have its own stereoisomerism, that could be the same or different than the stereoisomerism of the other double bonds of the molecule. Furthermore, compounds referred to herein may exist as atropisomers. All the stereoisomers including enantiomers, diastereoisomers, geometric isomers and atropisomers of the compounds referred to herein, and mixtures thereof, are considered within the scope of the present invention.

The present invention is directed to combinations of PLD with a further agent or agents.

Combination therapies may have advantages over monotherapies. Using combination therapies can avoid or minimise the emergence of drug resistant viruses. Combination therapies may potentiate antiviral activity. These effects enhance the chance to improve clinical outcome. In embodiments, agents may be selected to tackle distinct steps of the viral life cycle. In one embodiment, an agent that inhibits viral entry or viral-cell fusion may be combined with an agent that acts post-viral entry. Alternatively, the agents may tackle the same step—for example, the agent(s) combined with PLD may target viral entry only or post-viral entry only.

In one embodiment, the combination agent has anti-inflammatory properties.

By "combination agent(s)", it is meant the one or more further agents as defined herein used in combination with PLD.

The combinations of the present invention are directed to antiviral uses of PLD and not oncology indications for which PLD is also approved.

The following agents have been identified as combination agents.

In one aspect, the combination agent inhibits viral entry or viral-cell fusion. SARS-CoV-2 has two routes of entry (1) via fusion with the plasma membrane (the "early pathway") or (2) via endocytosis and cellular cathepsins, which then cleave the viral spike protein triggering the fusion pathway and releasing the CoV genome (the "late pathway") into the cell cytoplasm. In one embodiment, more than one combination agent may be used to block both the early and late pathways.

Accordingly, in one embodiment, the combination agent inhibits plasma membrane fusion between the host cell plasma membrane and the virus. This will prevent delivery of the viral genome into the cell interior and the eventual production of new virions. Coronavirus membrane fusion occurs after receptor binding of the viral S protein so that both the viral membrane and host cell membrane are proximal to one another. However, the S-protein must first be cleaved by proteases (primed) to become fusion-competent. In one embodiment, the combination agent is an exogenous or transmembrane protease inhibitor, more preferably a serine protease inhibitor or serpin. Preferably, the protease inhibitor prevents or reduces cleavage of the viral S protein.

In an embodiment, the combination agent is selected from any one of arbidol, aprotinin, HAI-1, HAI-2, SFTI-1, ε-aminocaproic acid, 4-(2-aminoethyl)benzenesulfonylfluoride, p-aminobenzamidine, camostat (e.g. camostat mesylate), nafamostat (e.g. nafamostat mesylate), H-d-hTyr-Ala-4-Amba, BAPA, CVS-3983, IN-1, WX-UK1, mesupron, MI-432, MI-462, bromhexine, MI-1148, PF-429242, danoprevir, simeprevir, lomibuvir, daclatasvir, telaprevir, boceprevir, narlaprevir, trelagliptin, alogliptin, linagliptin, sitagliptin, saxagliptin, vildagliptin, alvelestat and gabexate.

In a further embodiment, the combination agent is a type II transmembrane serine protease (TTSP) inhibitor. The TTSP may be a soluble protease, such as TMPRSS11a. In another embodiment, the combination agent is a TMPRSS2 inhibitor. In a preferred embodiment, the agent is camostat (mesylate), bromhexine (hydrochloride), aprotinin or nafamostat.

In a further preferred embodiment, the combination agent is camostat. In another embodiment, the combination agent is arbidol.

Membrane fusion is also dependent on the lipid content of the viral and/or host cellular membrane. In a further embodiment, the combination agent may deplete cholesterol from the plasma membrane and/or disrupt the formation of lipid rafts. Accordingly, in one embodiment, the combination agent is a cholesterol depleting agent. Disrupting raft formation, in particular, may prevent viral docking and cellular entry. In one embodiment, the agent is selected from any one of fluvastatin, atorvastatin, lovastatin, pravastatin, simvastatin, gemfibrozil, methyl-beta cyclodextrin, beta-cyclodextrin, RAMEB, DIMEB, HPβCD and TRIMEB. In a preferred embodiment, the agent is methyl-beta cyclodextrin, which depletes cholesterol from the plasma membrane and disrupts the formation of lipid rafts, which may contain the SARS-CoV-2 docking membrane protein, ACE2.

In another embodiment, the combination agent may inhibit a cholesterol transporter to inhibit intracellular cholesterol transport. In a preferred embodiment, the agent is itraconazole.

In another embodiment, the combination agent may prevent or inhibit ganglioside biosynthesis to prevent viral binding. In an embodiment, the combination agent is a ganglioside biosynthesis pathway inhibitor. Ganglioside biosynthesis pathway inhibitors inhibit enzymes (such as serine palmitoyltransferase, sphingomyelin synthase and Cer synthase) that mediate sphingolipid biosynthesis leading to a decrease in the infectivity of viruses. In an embodiment, the agent is selected from any one of ISP-1, myriocin, NA255, D609, SPK-601, MS-209, N-butyldeoxynojirimycin (NB-DNJ) and D,L-threo-1-phenyl-2-decanoylamino-3-morpholino-1-propanol (PDMP). In a preferred embodiment, the agent is NB-DNJ, which is an inhibitor of the GM1 ganglioside pathway.

In another embodiment, the combination agent inhibits endocytosis, and more preferably, clathrin-mediated endocytosis. In one embodiment, the combination agent is a clathrin-mediated endocytosis inhibitor. Clathrin-mediated endocytosis inhibitors interfere with the clathrin-mediated endocytosis process in a number of ways. For example, an agent may; translocate clathrin and adaptor protein 2 (AP2) from the cell surface to intracellular endosomes; block the entry of virions into coated-pit structures; affect the function of clathrin-coated vesicles (e.g. by raising endosomal pH and thereby interfering with the viral fusion process); affect the formation of clathrin-coated vesicles; interfere with the proton gradient; block the GTPase activity of dynamin (e.g. dynamin I); interfere with binding of clathrin box ligands to the N-terminal domain of clathrin (thereby stalling clathrin-coated pit dynamics and hence interfering with clathrin-mediated endocytosis).

In an embodiment, the combination agent is selected from any one of chlorpromazine, monodansylcadavarine, amantadine, rimantadine, phenylarsine oxide, hydroxychloroquine, chloroquine, monensin, phenothiazines, dynasore, dynoles, dyngoes and pitstops (e.g. pitstop 1 and 2). In a preferred embodiment, the agent is hydroxychloroquine, chloroquine, amantadine or chlorpromazine. In a further preferred embodiment, the combination agent is hydroxychloroquine or chloroquine or a chloroquine derivative, which raises endosomal pH and interferes with the viral fusion process. In a further preferred embodiment, the combination agent is hydroxychloroquine.

In an embodiment, the combination agent reduces viral entry by interfering with the AP2-associated protein kinase 1 (AAK1), a pivotal regulator of clathrin-mediated endocytosis in epithelial cells. Inhibition of AAK1 has been shown to reduce viral infection. Known inhibitors of AAK1 include JAK inhibitors. Accordingly, in one embodiment, the combination agent is a JAK inhibitor. In an embodiment, the combination agent is selected from any one of tofacitinib, CYT387, baricitinib, ruxolitinib, TG101348, lestaurtinib, AZD1480, R348, VX-509, GLPG0634, GSK2586184, AC-430, pacritinib and BMS-911543. In a preferred embodiment, the agent is tofacitinib, which has a particularly strong affinity for AAK1.

In another embodiment, the combination agent is a protease inhibitor and more preferably, a cysteine protease inhibitor. The protease inhibitor interferes with the proteolytic processing of viruses, particularly the S protein, during entry into host cells. In a preferred embodiment, the protease is an endosomal protease, and particularly an endosomal protease, preferably one that is activated by the low pH of the endosomal environment. More preferably, the combination agent is a cathepsin inhibitor. Alternatively, the inhibitor is a calpain inhibitor.

In an embodiment, the combination agent is a cathepsin inhibitor, a cathepsin B inhibitor, a cathepsin L inhibitor, a calpain inhibitor, a combined calpain and cathepsin B inhibitor, a pan cathepsin B/L inhibitor. In an embodiment, the agent is selected from any one of odanacatib, cathepsin inhibitor 1, E64, E64d (aloxistatin), MG-132, PD151746, leupeptin, Z-FA-FMK, loxistatin acid, CA-074, MDL28170, simeprevir, boceprevir, narlaprevir, MG-132, calpeptin, MDL28170 (Calpain inhibitor III), Calpain inhibitor VI, Calpain inhibitor I, MG-115, Calpain inhibitor II, Calpain inhibitor XII, PSI, GC-376 and rupintrivir. In a preferred embodiment, the agent is MDL28170 (which is a combined calpain and cathepsin B inhibitor), E64d (which is a pan cathepsin B/L inhibitor acting downstream once viruses are internalized in endosomes) or CA-074 (which is a cathepsin B inhibitor). In a preferred embodiment, the combination agent is MDL28170.

Following viral entry, the viral RNA is released into the cytoplasm, where its genome is translated and cleaved to generate new virions. Accordingly, in another aspect, the combination agent inhibits the steps of viral infection, such as viral replication, that are post-viral cell entry.

In an embodiment, the combination agent is an RNA polymerase inhibitor. RNA polymerase inhibitors prevent replication of the viral genome. Some RNA polymerase inhibitors may act as a prodrug and become phosphorylated in vivo. These RNA polymerase inhibitors (or their phosphorylated analogues) act as competitive, non-competitive, uncompetitive or suicide inhibitors of RNA polymerase. In an embodiment, the agent is selected from any one of sofosbuvir, sofosbuvir+ribavirin, sofusbuvir+ribavirin+PegIFNα, sofosbuvir+ledipasvir (Harvoni), sofosbuvir+simeprevir, sofosbuvir+daclatavir, ombitasvir+dasabuvir+paritaprevir+ritonavir (Viekira Pak), dasabuvir, ribavirin, favipiravir, remdesivir, beclabuvir, deleobuvir, filibuvir, radalbuvir and setrobuvir. In a preferred embodiment, the combination agent is remdesivir or favipiravir. In a further preferred embodiment, the agent is remdesivir.

In an embodiment, the combination agent is a HIV-1 protease inhibitor. HIV-1 protease inhibitors interfere with cleavage of Gag and Gag-Pol polyprotein precursor encoded by the HIV-1 virus genome. This interference limits viral maturation by preventing the production of mature active proteins such as protease, reverse transcriptase (p51), RNase H (p15), and integrase. In an embodiment, the combination agent is selected from any one of tipranavir, darunavir, darunavir+cobicistat, amprenavir, fosamprenavir, lopinavir, lopinavir-ritonavir, atazanavir, atazanavir+cobicistat, saquinavir, indinavir, ritonavir, nelfinavir (e.g. nelfinavir mesylate hydrate), SPI-256 and GS 8374. In a preferred embodiment, the agent is nelfinavir mesylate hydrate, lopinavir, tipranavir, amprenavir or darunavir. In a further preferred embodiment, the combination agent is nelfinavir mesylate hydrate.

In an embodiment, the combination agent is an IFN stimulated antiviral protein. IFNs are a multigene family of inducible cytokines and possess antiviral activity. IFNs are grouped into two types: Type I IFNs (also known as viral IFNs), which include IFN-α (leukocyte), IFN-β (fibroblast) and IFN-ω; and Type II IFNs (also known as immune IFN, or IFN-γ). IFNs target IFN-induced proteins within single cells such as: PKR kinase, which inhibits translation initiation through the phosphorylation of protein synthesis initiation factor eIF-2α; the OAS synthetase family and RNase L nuclease, which mediate RNA degradation; the family of Mx protein GTPases, which appear to target viral nucleocapsids and inhibit RNA synthesis; and ADAR, which edits double-stranded RNA by deamination of adenosine to yield inosine. IFN-induced expression of MHC class I and class II antigens and nitric oxide synthase also contribute to the antiviral responses observed within whole animals. In an embodiment, the agent is IFN-α, such as IFN-α2α (Roferon A), IFN-α2b (Intron A), consensus IFN-αcon (Infergen), human leukocyte-derived IFN-αn3 (Alferon N), human lymphoblastoid-derived IFN-αn1 (Wellferon), Peg-IFN-α2α (Pegasys) and Peg-IFN-α2b (PEG-Intron); IFN-β, such as Avonex and Betaseron; and IFN-γ, such as Actimmune. In a preferred embodiment, the combination agent is interferon 2-alpha or interferon gamma.

In an embodiment, the combination agent is a TLR 7 agonist, preferably vesatolimod.

In an embodiment, the combination agent is a PPARα receptor agonist. PPARα receptor agonists exhibit anti-viral as well as anti-inflammatory properties. In an embodiment, the combination agent is selected from any one of gemfibrozil, clofibrate, WY14643, oleoylethanolamide, palmitoylethanolamide, fenofibrate, bezafibrate and pemafibrate. In a preferred embodiment, the agent is fenofibrate.

In an embodiment, the combination agent inhibits the activity of the coronavirus replication complex. In one embodiment, the combination agent inhibits the viral proteinase, $M^{pro}$—also known as 3C-like proteinase ($3CL^{pro}$). In one embodiment, the proteinase is inhibited by a calpain inhibitor.

In an embodiment, the combination agent is a glucocorticoid. Glucocorticoids have been shown to inhibit viral replication of SARS-CoV-2. In an embodiment, the combination agent is selected from any one of paramethasone, prednylidene, triamcinolone, medrysone, amcinonide, fluorometholone, beclomethasone (e.g. beclomethasone dipropionate), betamethasone (e.g. betamethasone phosphate), prednisone (e.g. prednisone acetate), rimexolone, clobetasol (e.g. clobetasol propionate), fluocinonide, ciclesonide, fluprednidene (e.g. fluprednidene acetate), fluocortolone, difluocortolone, dexamethasone (e.g. dexamethasone isonicotinate), fluticasone (e.g. fluticasone furoate), meprednisone, deflazacort, cortivazol, cloprednol, mometasone (e.g. mometasone furoate), cortisone (e.g. cortisone acetate), prednisolone (e.g. prednisolone phosphate, prednisolone hemisuccinate), methylprednisolone (e.g. methylprednisolone hemisuccinate), clocortolone (e.g. clocortolone acetate), melengestrol (e.g. melengestrol acetate) and halometasone. In a preferred embodiment, the combination agent is ciclesonide. For the avoidance of doubt, the present invention allows for the additional administration of a corticosteroid (preferably dexamethasone) in addition to the combination agents of the present invention. If the combination agent is a glucocorticoid (for example ciclesonide), an additional corticosteroid (preferably dexamethasone) may also be administered as defined herein.

In an embodiment, the combination agent is an agent which inhibits viral replication.

In an embodiment, the combination agent is an agent which inhibits viral entrance.

In a preferred embodiment, PLD is combined with one or more further agents selected from agent(s) that inhibits viral entry, inhibits viral-cell fusion, inhibits endocytosis or inhibits viral replication. In particular, PLD or a pharmaceutically acceptable salt or stereoisomer thereof is used in combination with one or more further CoV antiviral agent(s) selected from calpain, cathepsin or calpain/cathepsin inhibitors, RNA polymerase inhibitors, clathrin-mediated endocytosis inhibitors, HIV-1 protease inhibitors, serine protease inhibitors, TMPRSS2 inhibitors, IFN stimulated antiviral proteins, PPARα receptor agonists, cholesterol transporter inhibitors, intracellular cholesterol transport inhibitors, ganglioside biosynthesis pathway inhibitors, cholesterol depleting agents, glucocorticoids, agents that inhibits viral fusion with host cell membranes and JAK inhibitors.

In a further preferred embodiment, PLD is combined with one or more further agents selected from calpain, cathepsin or calpain/cathepsin inhibitors, RNA polymerase inhibitors, clathrin-mediated endocytosis inhibitors, HIV-1 protease inhibitors, serine protease inhibitors, TMPRSS2 inhibitors, IFN stimulated antiviral proteins and PPARα receptor agonists. Specific agents may include MDL 28170, remdesivir, hydroxychloroquine, nelfinavir mesylate hydrate, chloroquine, interferon 2α, interferon-γ, and fenofibrate.

In a preferred embodiment of the combination of the present invention, the molar ratio of PLD or a pharmaceutically acceptable salt or stereoisomer thereof to further agent in said combination is from 1:1000 to 1000:1, or from 1:700 to 700:1, 1:500 to 500:1, 1:300 to 300:1, 1:100 to 100:1, or 1:50 to 50:1.

Compounds of the invention may be used in pharmaceutical compositions having biological/pharmacological activity for the treatment of the above mentioned infections and associated conditions. These pharmaceutical compositions comprise a compound of the invention together with a pharmaceutically acceptable carrier. The term "carrier" refers to a diluent, adjuvant, excipient or vehicle with which the active ingredient is administered. Suitable pharmaceutical carriers are described in "Remington's Pharmaceutical Sciences" by E. W. Martin, 1995. Examples of pharmaceutical compositions include any solid (tablets, pills, capsules, granules, etc.) or liquid (solutions, suspensions, emulsions, etc.) compositions for oral, topical or parenteral administration. Pharmaceutical compositions containing compounds of the invention may be delivered by liposome or nanosphere encapsulation, in sustained release formulations or by other standard delivery means.

An exemplary composition for PLD is in the form of powder for solution for infusion. For example, compositions as described in WO9942125. For example, a lyophilised preparation of a compound of the invention including water-soluble material and secondly a reconstitution solution of mixed solvents. A particular example is a lyophilised preparation of PLD and mannitol and a reconstitution solution of mixed solvents, for example PEG-35 castor oil, ethanol and water for injections. Each vial, for example may contain 2 mg of PLD. After reconstitution, each mL of reconstituted solution may contain: 0.5 mg of PLD, 158 mg of PEG-35 castor oil, and ethanol 0.15 mL/mL.

Exemplary composition for the other active agents in the combination (i.e. not PLD) will depend on the active agent in question.

In embodiments, there is provided a kit comprising a combination including PLD according to the present invention and, optionally, instructions for treating a patient. Typically, a kit can comprise PLD or a pharmaceutically acceptable salt or stereoisomer thereof and the further combination agent(s) together with instructions for treating a patient. Each active agent can be provided in a suitable container. The kit may further comprise a delivery system. The kit may comprise PLD together with instructions for the combination use with a further agent or agents according to the present invention. The kit may comprise further agent or agents according to the present invention together with instructions for the combination use with PLD.

The instructions may advise administering PLD according to the present invention in combination with a further agent according to the present invention for the treatment of CoV infection or COVID-19. The kit may instruct that the combinations be administered concurrently, sequentially or separately.

The specific combination may be selected based on a variety of factors, including the activity of the specific compounds employed, the particular formulations being used, the mode of application, the age, body weight, general health, sex, diet, time of administration, rate of excretion, drug combination, reaction sensitivities, identified or potential resistance and the severity of the particular disease or condition being treated.

The combinations of the present inventions may be adapted for administration concurrently, sequentially or separately.

The specific dosage and treatment regimen for any particular agent may be varied and will also depend upon a variety of factors, including the activity of the specific compounds employed, the particular formulations being used, the mode of application, the age, body weight, general health, sex, diet, time of administration, rate of excretion, drug combination, reaction sensitivities, identified or potential resistance and the severity of the particular disease or condition being treated.

In embodiments of the invention, the dosage regimen for the combination agent(s) (i.e. the agent(s) other than PLD) will be administered according to the appropriate dosing regimen for that agent.

In embodiments of the invention, PLD or a pharmaceutically acceptable salt or stereoisomer thereof may be administered according to a dosing regimen of a daily dose.

In embodiments of the invention, PLD or a pharmaceutically acceptable salt or stereoisomer thereof may be administered according to a dosing regimen of a once daily dose.

In further embodiments, PLD or a pharmaceutically acceptable salt or stereoisomer thereof may be administered according to a dosing regimen of a daily dose for 10 days, 9 days, 8 days, 7 days, 6 days, 5 days, 4 days, 3 days, 2 days or 1 day. Preferred regimen is 2-5 days, or 3-5 days, or 3, 4 or 5 days, most preferably 3 days or 5 days.

The dose may be a dose of 5 mg a day or less, 4.5 mg a day or less, 4 mg a day or less, 3.5 mg a day or less, 3 mg a day or less, 2.5 mg a day or less or 2 mg a day or less.

Particular doses include 0.5 mg/day, 1 mg/day, 1.5 mg/day, 2 mg/day, 2.5 mg/day, 3 mg/day, 3.5 mg/day, 4 mg/day, 4.5 mg/day, or 5 mg/day. Preferred doses are 1 mg/day, 1.5 mg/day, 2 mg/day and 2.5 mg/day.

In further embodiments, PLD or a pharmaceutically acceptable salt or stereoisomer thereof may be administered according to a total dose of 1-50 mg, 1-40 mg, 1-30 mg, 1-20 mg, 1-15 mg, 3-15 mg, 3-12 mg, 4-12 mg, 4-10 mg, or 4.5-10 mg. Total doses may be 4 mg, 4.5 mg, 5 mg, 5.5 mg, 6 mg, 6.5 mg, 7 mg, 7.5 mg, 8 mg, 8.5 mg, 9 mg, 9.5 mg or 10 mg. Preferred total doses are 4.5 mg, 5 mg, 6 mg, 7.5 mg, 8 mg, 9 mg or 10 mg. The total dose may be split over 1, 2, 3, 4, 5, 6, 7, 8, 9 or 10 days, preferably 3 days or 5 days.

In a particular embodiment, PLD or a pharmaceutically acceptable salt or stereoisomer thereof may be administered according to a dosing regimen of a once daily dose for 5 days, at a dose of 2.5 mg a day or less.

In a further embodiment, PLD or a pharmaceutically acceptable salt or stereoisomer thereof may be administered according to a dosing regimen of a once daily dose for 5 days, at a dose of 2 mg a day or less.

In a further embodiment, PLD or a pharmaceutically acceptable salt or stereoisomer thereof may be administered according to a dosing regimen of a once daily dose for 3 days, at a dose of 1.5 mg a day or less.

In a further embodiment, PLD or a pharmaceutically acceptable salt or stereoisomer thereof may be administered according to a dosing regimen of a once daily dose for 3 days, at a dose of 2 mg a day or less.

In a further embodiment, PLD or a pharmaceutically acceptable salt or stereoisomer thereof may be administered according to a dosing regimen of a once daily dose for 3 days, at a dose of 2.5 mg a day or less.

In a further embodiment, PLD or a pharmaceutically acceptable salt or stereoisomer thereof may be administered according to a dosing regimen of a once daily dose for 3 days, at a dose of 1.5 mg a day.

In a further embodiment, PLD or a pharmaceutically acceptable salt or stereoisomer thereof may be administered according to a dosing regimen of a once daily dose for 3 days, at a dose of 2.0 mg a day.

In a further embodiment, PLD or a pharmaceutically acceptable salt or stereoisomer thereof may be administered according to a dosing regimen of a once daily dose for 3 days, at a dose of 2.5 mg a day.

In a further embodiment, PLD or a pharmaceutically acceptable salt or stereoisomer thereof may be administered according to a dosing regimen of a once daily dose for 3 days, at a dose of 1.5 to 2.5 mg a day.

An alternative regimen is a single dose on day 1 for PLD or a pharmaceutically acceptable salt or stereoisomer thereof. The single dose regiment may be particularly suited to the treatment of: mild infection; reducing complications associated with CoV infection, including hospitalization, ICU and death; prophylaxis, reduction, avoidance or treatment of COVID persistent, long COVID, post-COVID syndrome; and/or reducing the infectivity of CoV patients. The single dose of PLD may be 1-10 mg, 4-10 mg, 4.5-10 mg; 4 mg, 4.5 mg, 5 mg, 5.5 mg, 6 mg, 6.5 mg, 7 mg, 7.5 mg, 8 mg, 8.5 mg, 9 mg, 9.5 mg or 10 mg; preferably 4.5 mg, 5 mg, 6 mg, 7.5 mg, 8 mg, 9 mg or 10 mg; more preferably 5-9 mg, 6.5-8.5 mg, 7-8 mg or 7.5 mg.

In a further embodiment, PLD or a pharmaceutically acceptable salt or stereoisomer thereof may be administered according to the present invention, wherein the compounds of the present invention are administered with an additional corticosteroid. Preferably the corticosteroid is dexamethasone.

The corticosteroid may be administered daily PLD or a pharmaceutically acceptable salt or stereoisomer thereof. Administration may be sequential, concurrent or consecutive. The corticosteroid may be further administered on the days following administration of PLD or a pharmaceutically acceptable salt or stereoisomer thereof. By way of example, with a 3 day dosing regimen, the corticosteroid may be administered on days 1-3 and then further administered daily for 3, 4, 5, 6, 7, 8, 9 or 10 or more further days.

In a particular embodiment, the corticosteroid may be administered is administered on days 1-3 as an intravenous administration and then on days 6-10 as an oral administration. In a further embodiment, the dosage of corticosteroid may be higher during the co-administration phase with PLD or a pharmaceutically acceptable salt or stereoisomer thereof, and is lowered during the subsequent days.

Particular dosing schedules for the PLD component of the combination include:

PLD 1.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

PLD 2.0 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

PLD 2.5 mg/day intravenous (IV) combined with dexamethasone 6.6 mg/day IV on Days 1 to 3, followed by dexamethasone 6 mg/day oral administration (PO)/IV from Day 4 and up to Day 10 (as per physician judgement according to patient clinical condition and evolution).

In an embodiment, to avoid administration-related infusion reactions patients may receive the following medications 20 to 30 minutes prior to starting the infusion with PLD or a pharmaceutically acceptable salt or stereoisomer thereof:

Ondansetron 8 mg IV (or equivalent)

Diphenhydramine hydrochloride 25 mg IV (or equivalent)

Ranitidine 50 mg IV (or equivalent)

Dexamethasone 6.6 mg IV (which is included in the schedule above)

Additionally, on Days 4 and 5 patients treated with compounds according to the present invention may receive ondansetron 4 mg twice a day PO.

Doses of dexamethasone, ondansetron and ranitidine are herein defined on the basis of the base form. The dose of diphenhydramine hydrochloride is given on the basis of the hydrochloride salt. Doses of compounds of the invention are given on the basis of the base form.

The daily doses may be administered as an infusion. The infusion may be a 1 hour infusion, a 1.5 hour infusion, a 2 hour infusion, a 3 hour infusion or longer. Preferably, the infusion is 1.5 hours.

In certain embodiments, the dose may be administered according to a regimen which uses a loading dose and a maintenance dose. Loading/maintenance doses according to the present invention includes:

- a loading dose of 2.5 mg for day 1, and followed by a maintenance dose of 2 mg/day for subsequent days;
- a loading dose of 2.5 mg for day 1, and followed by a maintenance dose of 1.5 mg/day for subsequent days;
- a loading dose of 2.5 mg for day 1, and followed by a maintenance dose of 1 mg/day for subsequent days;
- a loading dose of 2.5 mg for day 1, and followed by a maintenance dose of 0.5 mg/day for subsequent days;
- a loading dose of 2 mg for day 1, and followed by a maintenance dose of 1.5 mg/day for subsequent days;
- a loading dose of 2 mg for day 1, and followed by a maintenance dose of 1 mg/day for subsequent days;
- a loading dose of 2 mg for day 1, and followed by a maintenance dose of 0.5 mg/day for subsequent days;
- a loading dose of 1.5 mg for day 1, and followed by a maintenance dose of 1 mg/day for subsequent days;
- a loading dose of 1.5 mg for day 1, and followed by a maintenance dose of 0.5 mg/day for subsequent days; and
- a loading dose of 1 mg for day 1, and followed by a maintenance dose of 0.5 mg/day for subsequent days.

According to a further embodiment, the daily dose may be reduced in the final day or days of the regimen.

According to a further embodiment, if the daily dose is 2 mg, the dose may be reduced to 1 mg on days 4 and 5.

Particular regimens include:

- 1 mg of PLD administered as a 1.5-hour infusion, once a day for 5 consecutive days. (total dose 5 mg);
- 2 mg of PLD administered as a 1.5-hour infusion, once a day for 5 consecutive days. At the discretion of the researcher, the dose may be reduced to 1 mg/day on days 4 and 5 (total dose 8-10 mg);
- 1.5 mg of PLD administered as a 1.5-hour infusion, once a day for 3 consecutive days. (total dose 4.5 mg);
- 2 mg of PLD administered in 1.5 hour infusion, once a day for 3 consecutive days. (total dose 6 mg); and
- 2.5 mg of PLD administered as a 1.5-hour infusion, once a day for 3 consecutive days. (total dose 7.5 mg).

A single dose regimen for the PLD component of the combination includes:

- PLD administered as a 1.5-hour infusion, once on day 1 at a dose of 1-10 mg, 4-10 mg, 4.5-10 mg, 4 mg, 4.5 mg, 5 mg, 5.5 mg, 6 mg, 6.5 mg, 7 mg, 7.5 mg, 8 mg, 8.5 mg, 9 mg, 9.5 mg or 10 mg, preferably 4.5 mg, 5 mg, 6 mg, 7.5 mg, 8 mg, 9 mg or 10 mg, more preferably 5-9 mg, 6.5-8.5 mg, 7-8 mg or most preferably 7.5 mg.
- The single dose regimen may further include the following prophylactic medications 20-30 minutes prior to PLD infusion:

Diphenhydramine hydrochloride 25 mg i.v.,

Ranitidine 50 mg i.v.

Dexamethasone 6.6 mg intravenously.

Ondansetron 8 mg i.v. in slow infusion of 15 minutes

Ondansetron 4 mg orally may be given every 12 hours for 3 days after PLD administration to relieve drug-induced nausea and vomiting. If PLD is administered in the morning the patient may receive the first dose of ondansetron in the afternoon.

According to further embodiments, patients may be selected for treatment with PLD based on clinical parameters and/or patient characteristics. Suitable parameters may be measurements disclosed in the present application.

As highlighted above the dosage regimen for the combination agent(s) (i.e. the agent(s) other than PLD) will be administered according to the appropriate dosing regimen for that agent.

The regimens and doses outlined above may apply to methods of treatment and uses as defined herein.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

EXAMPLES

PLD can be made according to WO 02/02596 or as elsewhere disclosed in the literature.

Material & Methods

Cell Cultures. Vero E6 cells (ATCC CRL-1586) were cultured in Dulbecco's modified Eagle medium, (DMEM; Lonza) supplemented with 5% fetal calf serum (FCS; EuroClone), 100 U/mL penicillin, 100 μg/mL streptomycin, and 2 mM glutamine (all ThermoFisher Scientific).

Virus Isolation, Titration and Sequencing.

SARS-CoV-2 virus was isolated from a nasopharyngeal swab collected from an 89-year-old male patient giving informed consent and treated with Betaferon and hydroxychloroquine for 2 days before sample collection. The swab was collected in 3 mL medium (Deltaswab VICUM) to reduce viscosity and stored at −80° C. until use. Vero E6 cells were cultured on a cell culture flask (25 $cm^2$) at $1.5\times10^6$ cells overnight prior to inoculation with 1 mL of the processed sample, for 1 h at 37° C. and 5% $CO_2$. Afterwards, 4 mL of 2% FCS-supplemented DMEM were supplied and cells were incubated for 48 h. Supernatant was harvested, centrifuged at 200×g for 10 min to remove cell debris and stored at −80° C. Cells were assessed daily for cytopathic effect and the supernatant was subjected to viral RNA extraction and specific RT-qPCR using the SARS-CoV-2 UpE, RdRp and N assays (Corman et al., 2020). The virus was propagated for two passages and a virus stock was prepared collecting the supernatant from Vero E6.

Viral RNA was extracted directly from the virus stock using the Indimag Pathogen kit (Indical Biosciences) and transcribed to cDNA using the PrimeScript™ RT reagent Kit (Takara) using oligo-dT and random hexamers, according to the manufacturer's protocol. DNA library preparation was performed using SWIFT amplicon SARS-CoV-2 panel (Swift Biosciences). Sequencing ready libraries where then loaded onto Illumina MiSeq platform and a 300 bp paired-end sequencing kit. Sequence reads were quality filtered and adapter primer sequences were trimmed using trimmomatic. Amplification primer sequences were removed using cut-adapt (Martin, 2011). Sequencing reads were then mapped against coronavirus reference (NC_045512.2) using bowtie2 tool (Langmead, B. and Salzberg, S, 2012). Consensus genomic sequence was called from the resulting alignment at a 18×1800×879 average coverage using samtools (Li et al., 2009). Genomic sequence was deposited at GISAID repository (http://gisaid.org) with accession ID EPI_ ISL_510689.

Antivirals & compounds. PLD was used at concentrations ranging from 100 μM to 0.0512 nM at ⅕ serial dilutions, and also assayed from 10 μM to 0.5 nM at ⅓ dilutions. When PLD and other drugs were combined, each one was added at a 1:1 molar ratio at a concentration ranging from 100 μM to 0.0512 nM at ⅕ serial dilutions, and also assayed from 10 μM to 0.5 nM at ⅓ dilutions.

Antiviral activity. Increasing concentrations of antiviral compounds were added to Vero E6 cells together with $10^{18}$ $TCID_{50}$/mL of SARS-CoV-2, a concentration that achieves a 50% of cytopathic effect. Non-exposed cells were used as negative controls of infection. In order to detect any drug-associated cytotoxic effect, Vero E6 cells were equally cultured in the presence of increasing drug concentrations, but in the absence of virus. Cytopathic or cytotoxic effects of the virus or drugs were measured at 3 days post infection, using the CellTiter-Glo luminescent cell viability assay (Promega). Luminescence was measured in a Fluoroskan Ascent FL luminometer (ThermoFisher Scientific).

$IC_{50}$ calculation and statistical analysis. Response curves of compounds or their mixes were adjusted to a non-linear fit regression model, calculated with a four-parameter logistic curve with variable slope. Cells not exposed to the virus were used as negative controls of infection and set as 100% of viability, and used to normalize data and calculate the percentage of cytopathic effect. Statistical differences from 100% were assessed with a one sample t test. All analyses and figures were generated with the GraphPad Prism v8.0b Software.

Antiviral activity for PLD was investigated for SARS-CoV-2. PLD was also investigated in combination with other antiviral agents.

SARS-CoV-2 entry is believed to require viral binding and spike protein activation via interaction with the cellular receptor ACE2 and cellular protease, a mechanism favoured by viral internalization via endocytosis. Interference with either of these initial processes has been shown to decrease SARS-CoV-2 entry and infectivity. In addition, SARS-CoV-2 may enter cells via endocytosis and accumulate in endosomes where cellular cathepsins can also prime the spike protein and favour viral fusion upon cleavage.

Experiments were therefore conducted to determine the activity of PLD combinations with entry inhibitor compounds, which may have an effect before viral entry by impairing viral-cell fusion.

Furthermore, when SARS-CoV-2 fuses with plasma membrane or endosomal membranes, it triggers viral RNA release into the cytoplasm, where polyproteins are translated and cleaved by proteases. This leads to the formation of an RNA replicase-transcriptase complex that drives the production of negative-stranded RNA via both replication and transcription. Negative-stranded RNA drives transcription of positive RNA genomes and translation of viral nucleoproteins, which assemble in viral capsids at the cytoplasm. These capsids then bud into the lumen of ER-Golgi compartments, where viruses are finally released to the extracellular space by exocytosis. This gives rise to multiple steps of the viral cycle that may be susceptible to be targeted with different antiviral compounds in combination with PLD. Experiments were therefore conducted to determine the activity of PLD combinations with post-entry inhibitors.

Further antiviral inhibitors have different or unknown mechanisms of action. Experiments were therefore conducted to determine the activity of PLD combinations with antiviral activity of inhibitors with unknown mechanism of action.

Example 1—Cytopathic Effect on Vero E6 Cells Exposed to PLD and its Combinations with Dolquine, Remdesivir, MDL28170 and Nelfinavir Mesylate Hydrate Antiviral activity for PLD is shown in FIG. 1, which shows the cytopathic effect on Vero E6 cells exposed to a fixed concentration of SARS-CoV-2 in the presence of increasing concentrations of PLD. PLD was used at a concentration ranging from 10 μM to 0.5 nM at ⅓ dilutions. Non-linear fit to a variable response curve from one representative experiment with two replicates is shown (squares). The particular $IC_{50}$ value of this graph is indicated. Cytotoxic effect on Vero E6 cells exposed to increasing concentrations of drugs in the absence of virus is also shown (circles).

A constant concentration of a clinical isolate of SARS-CoV-2 (ID EPI_ISL_418268) was mixed with increasing concentrations of PLD and added to Vero E6 cells. To control for drug-induced cytotoxicity, Vero E6 were also cultured with increasing concentrations of PLD in the absence of SARS-CoV-2. PLD was able to inhibit viral-induced cytopathic effects (squares) at concentrations where no cytotoxic effects of the drug were observed (circles). The mean $IC_{50}$ value and SD of PLD in two experiments with two replicates each was 0.051±0.02 μM.

Figure 2:
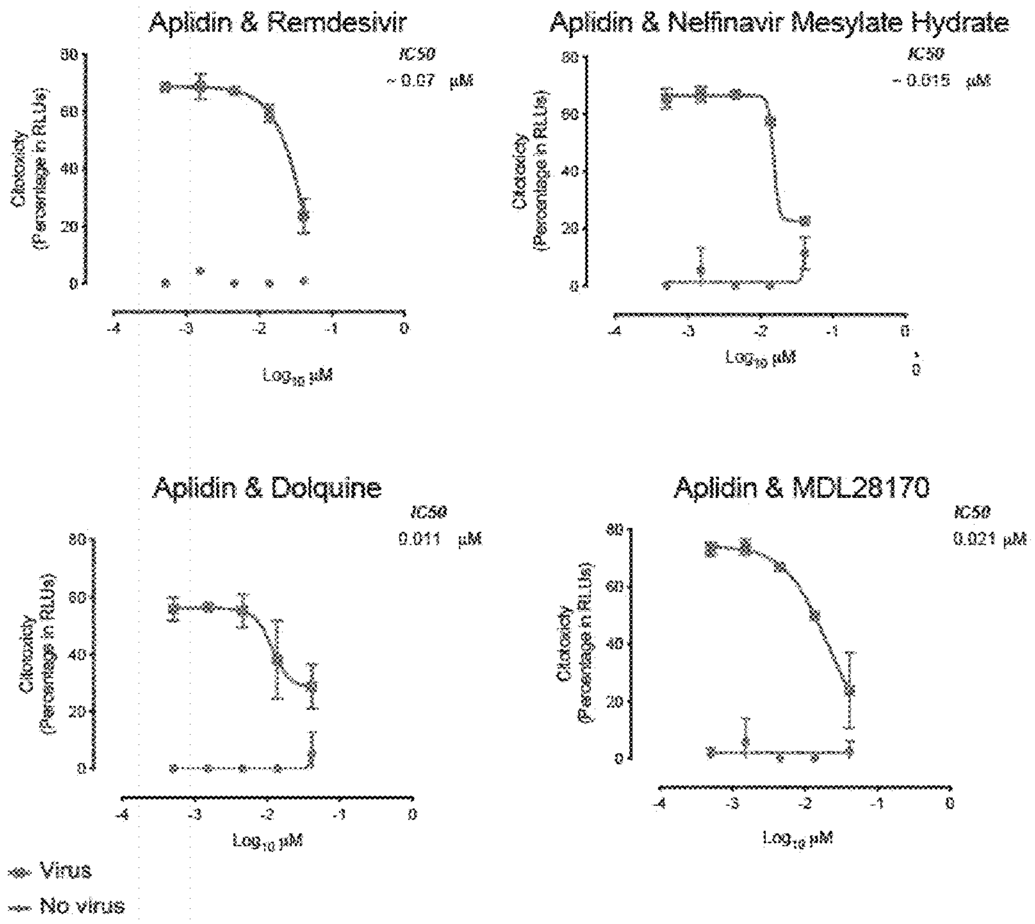
FIG. 2 shows the cytopathic effect on Vero E6 cells exposed to a fixed concentration of SARS-CoV-2 in the presence of increasing concentrations of PLD in combination with the indicated compounds, inhibiting viral replication (remdesivir and nelfinavir) or viral entrance (hydroxychloroquine and MDL28170). When combined, each drug was added at the same concentration. Drugs were used at a concentration ranging from 0.5 nM to 10 μM. Non-linear fit to a variable response curve from one representative experiment with two replicates is shown (squares), excluding data from drug concentrations with associated toxicity. Cytotoxic effect on Vero E6 cells exposed to decreasing concentrations of drugs in the absence of virus is also shown (circles).

PLD was tested in combination with other active antivirals. When combined, each drug was added at a 1:1 molar ratio at the same concentration. The combination of PLD and hydroxychloroquine showed the $IC_{50}$ of 0.011 μM. The results of this experiment are shown in FIG. 2. Importantly, no reduction in PLD activity is seen. Also importantly, no increase in toxicity is seen.

The combination of PLD and remdesivir showed an $IC_{50}$ of 0.07 μM. Again, importantly, no reduction in PLD activity is seen. Also importantly, no increase in toxicity was seen. The results of this experiment are shown in FIG. 2.

The combination of PLD and MDL28170 showed an $IC_{50}$ of 0.021 μM. Again, importantly, no reduction in PLD activity is seen. Also importantly, no increase in toxicity was seen. The results of this experiment are shown in FIG. 2.

The combination of PLD and Nelfinavir mesylate hydrate showed an $IC_{50}$ of 0.015 μM. Again, importantly, no reduction in PLD activity is seen. Also importantly, no increase in toxicity was seen. The results of this experiment are shown in FIG. 2.

The activity of remdesivir, hydroxychloroquine, MDL28170 and nelfinavir mesylate hydrate are shown in FIGS. 3-6.

Example 2—Antiviral Activity of Hydroxychloroquine Against SARS-CoV-2

Figure 3:
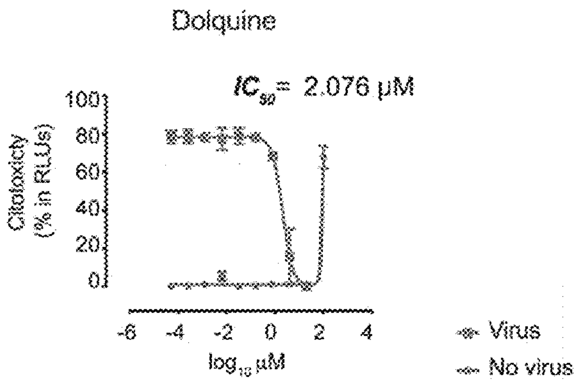
FIGS. 3-6 shows the cytopathic effect on Vero E6 cells exposed to a fixed concentration of SARS-CoV-2 in the presence of increasing concentrations of remdesivir, hydroxychloroquine, MDL28170 and nelfinavir mesylate.

Antiviral activity of Hydroxychloroquine is shown in FIG. 3, which shows the cytopathic effect on Vero E6 cells exposed to a fixed concentration of SARS-CoV-2 in the presence of increasing concentrations of hydroxychloroquine (Dolquine). Hydroxychloroquine used at a concentration ranging from 100 μM to 0.0512 nM. Non-linear fit to a variable response curve from one representative experiment with two replicates is shown (red squares), excluding data from drug concentrations with associated toxicity. The particular $IC_{50}$ value of this graph is indicated. Cytotoxic effect on Vero E6 cells exposed to increasing concentrations of drug in the absence of virus is also shown (grey circles).

The inhibitory effect of hydroxychloroquine (Dolquine) on SARS-CoV-2 induced cellular cytotoxicity on Vero E6 cells was confirmed in FIG. 3. A constant concentration of a clinical isolate of SARS-CoV-2 (ID EPI_ISL_418268) was mixed with increasing concentrations of hydroxychloroquine and added to Vero E6 cells. To control for drug-induced cytotoxicity, Vero E6 were also cultured with increasing concentrations of hydroxychloroquine in the absence of SARS-CoV-2. Hydroxychloroquine was able to inhibit viral-induced cytopathic effects (red squares) at concentrations where no cytotoxic effects of the drug were observed (grey circles). The mean $IC_{50}$ value and SD of this drug from at least three independent experiments with two replicates each was 9.3±11.1 μM.

Figure 4:
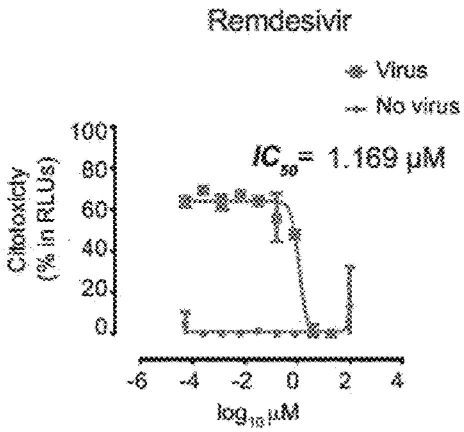

Example 3—Cytopathic Effect on Vero E6 Cells Exposed to a Fixed Concentration of SARS-CoV-2 in the Presence of Increasing Concentrations of Remdesivir Cytopathic effect on Vero E6 cells exposed to a fixed concentration of SARS-CoV-2 in the presence of increasing concentrations of remdesivir is shown in FIG. 4. Drug was used at a concentration ranging from 100 μM to 0.0512 nM. Non-linear fit to a variable response curve from one representative experiment with two replicates is shown (red squares), excluding data from drug concentrations with associated toxicity. The particular $IC_{50}$ value of this graph is indicated. Cytotoxic effect on Vero E6 cells exposed to increasing concentrations of drugs in the absence of virus is also shown (grey circles).

Drugs in combination were used at a concentration ranging from 100 μM to 0.0512 nM. Remdesivir was confirmed to have in vitro capacity to inhibit SARS-CoV-2-induced cytopathic effect on Vero E6 at concentrations where no cytotoxicity of the drug was observed. The mean $IC_{50}$ value and SD of this drug from at least three independent experiments with two replicates each was 2.16±4.1 μM.

Example 4—Cytopathic Effect on Vero E6 Cells Exposed to a Fixed Concentration of SARS-CoV-2 in the Presence of Increasing Concentrations of MDL28170

Figure 5:
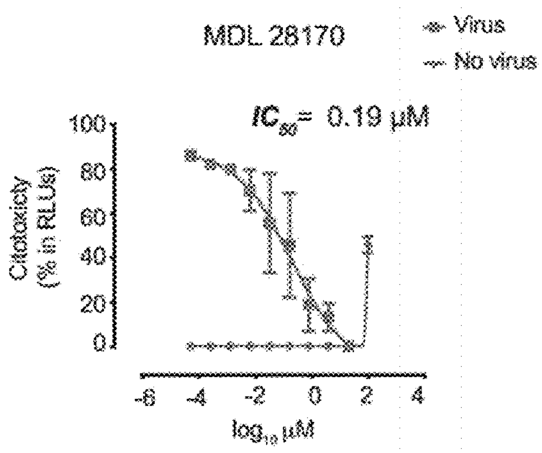

The cytopathic effect on Vero E6 cells exposed to a fixed concentration of SARS-CoV-2 in the presence of increasing concentrations of MDL 28170 Calpain inhibitor III is shown in FIG. 5. Drug was used at a concentration ranging from 100 μM to 0.0512 nM. Non-linear fit to a variable response curve from one representative experiment with two replicates is shown (red squares), excluding data from drug concentrations with associated toxicity. The particular $IC_{50}$ value of this graph is indicated. Cytotoxic effect on Vero E6 cells exposed to decreasing concentrations of drugs in the absence of virus is also shown (grey circles).

MDL 28170 was confirmed to have in vitro capacity to inhibit SARS-CoV-2-induced cytopathic effect on Vero E6 at concentrations where no cytotoxicity of the drug was observed. The mean $IC_{50}$ value and SD of this drug from at least two independent experiments with two replicates each was 0.14±0.06 μM.

Figure 6:
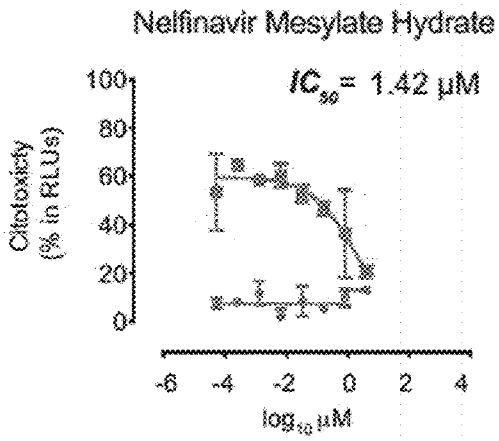

Example 5—Cytopathic Effect on Vero E6 Cells Exposed to Nelfinavir Mesylate Hydrate The cytotoxic effect on Vero E6 cells exposed to a fixed concentration of SARS-CoV-2 in the presence of increasing concentrations of protease inhibitors against HIV-1, nelfinavir mesylate hydrate. The results are shown in FIG. 6. Drug was used at a concentration ranging from 100 μM to 0.0512 nM. Non-linear fit to a variable response curve from one representative experiment with two replicates is shown (red squares), excluding data from drug concentrations with associated toxicity. The particular $IC_{50}$ value of this graph is indicated. Cytotoxic effect on Vero E6 cells exposed to increasing concentrations of drugs in the absence of virus is also shown (grey circles).

Nelfinavir mesylate hydrate was confirmed to have in vitro capacity to inhibit SARS-CoV-2-induced cytopathic effect on Vero E6 at concentrations where no cytotoxicity of the drug was observed.

These data show that PLD can be administered in combination with further agent(s), without reducing PLD activity. These data also show that PLD can be administered in combination with further agent(s) without adversely affecting toxicity. These important findings highlights the possibility of combining PLD with further agents to minimise or avoid the selection of resistant viruses.

PLD has been shown to be effective in combination with one or more further CoV antiviral agent(s) selected from agent(s) that inhibits viral entry, inhibits viral-cell fusion, inhibits endocytosis or inhibits viral replication. In particular, one or more further CoV antiviral agent(s) selected from calpain, cathepsin or calpain/cathepsin inhibitors, RNA polymerase inhibitors, clathrin-mediated endocytosis inhibitors, HIV-1 protease inhibitors, serine protease inhibitors, TMPRSS2 inhibitors, IFN stimulated antiviral proteins, PPARα receptor agonists, cholesterol transporter inhibitors, intracellular cholesterol transport inhibitors, ganglioside biosynthesis pathway inhibitors, cholesterol depleting agents, glucocorticoids, agents that inhibits viral fusion with host cell membranes and JAK inhibitors.

The antiviral agents described herein having antiviral activity tackle different steps of the viral life cycle and can therefore be considered for use in combination with PLD. These combinations retain efficacy and have acceptable cytotoxicity and may be used to minimize or avoid the emergence of resistant virus.

PLD in combination retains efficacy and retains acceptable cytotoxicity. The combinations disclosed herein are useful as antiviral combination agents in the arsenal against SARS-CoV-2 and COVID-19.

Example 6—Plasma Profile for PLD

Figure 7:
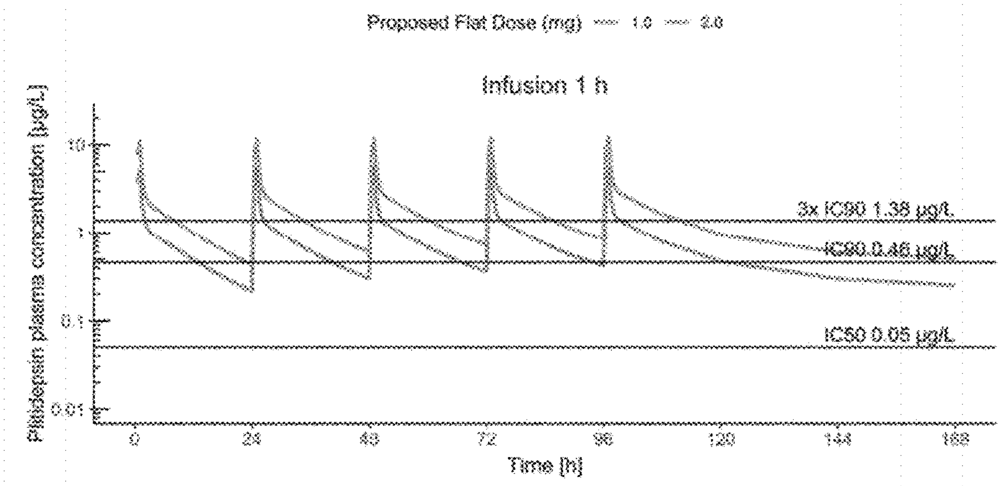
FIGS. 7 and 8 show total plasma concentration profiles vs. time predicted for dosing schedules and administration according to the present invention.

FIG. 7 illustrates the simulation of the total plasma plitidepsin concentration profiles vs. time after a daily dose (D1-D5) of 1.0 mg and 2.0 mg. The horizontal black lines represent the total plasma concentrations associated with the concentrations in lung equivalent to IC50, IC90 and 3×IC90 in vitro. With both dose levels (1.0 mg and 2.0 mg), plasma concentrations above IC50 would be obtained throughout the treatment period, and would remain above IC90 during most of the administration interval. Accumulation after five repeated administrations is minimal.

Figure 8:
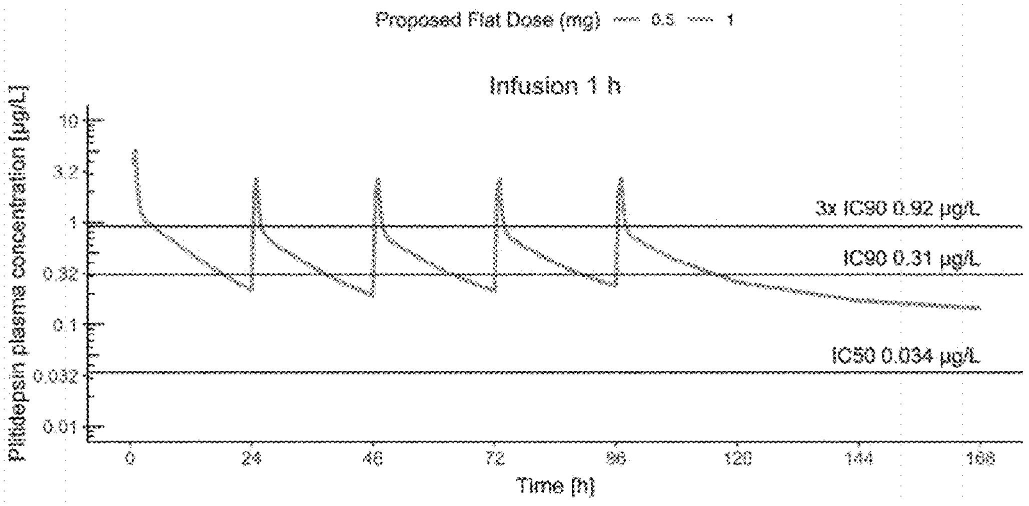

A further PLD dosage regimen is 1.5 mg daily for 5 days. A further regimen is illustrated in FIG. 8 which simulates plitidepsin total plasma concentrations associated to an initial flat dose of 1 mg (Day 1) given as a 1-h i.v. infusion, followed by daily doses of 0.5 mg (D2-D5). With this dose regimen, plitidepsin plasma concentrations are above the IC50 during the entire treatment period, and remains above IC90 during 18 and 14 hours, after 1 mg and 0.5 mg dose infusion, respectively. Notably, minimal accumulation after repeated administration is foreseen. This regimen provides a loading dose of 1 mg of plitidepsin given as 1-h i.v. infusion on the first day of treatment, followed by a maintenance dose of 0.5 mg once daily for 4 days.

Figure 9:
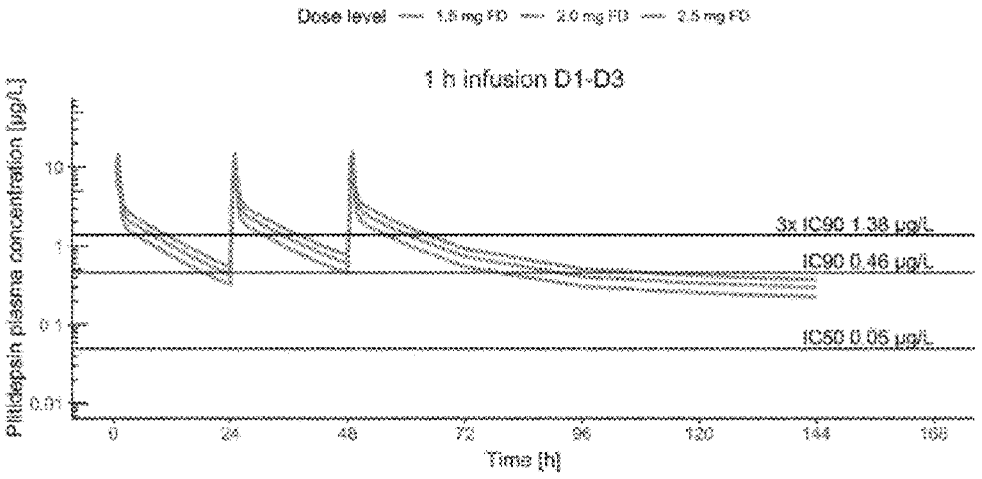
FIG. 9 shows total plasma concentration profiles vs. time predicted for further dosing schedules and administration according to the present invention.
Figure 10:
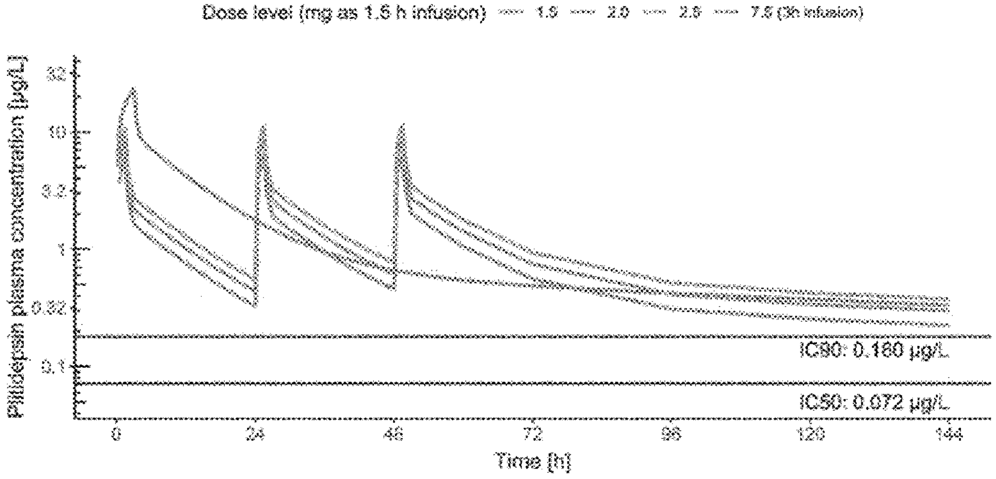
FIG. 10 shows total vs. plasma concentration profiles for single dose plitidepsin 7.5 mg and 1.5, 2.0 and 2.5 mg on day 1 to 3, using a 1.5 hour infusion.

FIG. 9 illustrates the simulation of the total plasma plitidepsin concentration profiles vs. time after a daily dose (D1-D3) of 1.5 mg, 2.0 mg and 2.5 mg. The horizontal black lines represent the total plasma concentrations associated with concentrations in lungs equivalent to IC50, IC90 and 3×IC90 in vitro. With all three dosage levels (1.5 mg, 2.0 mg and 2.5 mg), plasma concentrations above IC50 would be obtained throughout the treatment period and would remain above IC90 during most of the administration interval. Accumulation after three repeated administrations is minimal A validated plitidepsin population pharmacokinetic model (Nalda-Molina R, et al. Population pharmacokinetics meta-analysis of plitidepsin in cancer subjects. Cancer Chemother Pharmacol. 2009 June; 64(1):97-108. doi: 10.1007/s00280-008-0841-4) was used to confirm total plasma concentration will reach the estimated lung target concentrations. FIG. 10 shows the results and it can be seen that plasma concentrations above IC50 and IC90 can be obtained for more than 6 days.

REFERENCES

Boulware, D. R., Pullen, M. F., Bangdiwala, A. S., Pastick, K. A., Lofgren, S. M., Okafor, E. C., Skipper, C. P., Nascene, A. A., Nicol, M. R., Abassi, M., et al. (2020). A Randomized Trial of Hydroxychloroquine as Postexposure Prophylaxis for Covid-19. N. Engl. J. Med. NEJMoa2016638.

Caly, L., Druce, J. D., Catton, M. G., Jans, D. A., and Wagstaff, K. M. (2020). The FDA-approved Drug Ivermectin inhibits the replication of SARS-CoV-2 in vitro. Antiviral Res. 104787.

Cavalcanti, A. B., Zampieri, F. G., Rosa, R. G., Azevedo, L. C. P., Veiga, V. C., Avezum, A., Damiani, L. P., Marcadenti, A., Kawano-Dourado, L., Lisboa, T., et al. (2020). Hydroxychloroquine with or without Azithromycin in Mild-to-Moderate Covid-19. N. Engl. J. Med. NEJMoa2019014.

Elfiky, A. A. (2020). Ribavirin, Remdesivir, Sofosbuvir, Galidesivir, and Tenofovir against SARS-CoV-2 RNA dependent RNA polymerase (RdRp): A molecular docking study. Life Sci. 253, 117592.

Fantini, J., Di Scala, C., Chahinian, H., and Yahi, N. (2020). Structural and molecular modelling studies reveal a new mechanism of action of chloroquine and hydroxychloroquine against SARS-CoV-2 infection. Int. J. Antimicrob. Agents 105960.

Gassen, N. C., Papies, J., Bajaj, T., Dethloff, F., Emanuel, J., Weckmann, K., Heinz, D. E., Heinemann, N., Lennarz, M., Richter, A., et al. (2020). Analysis of SARS-CoV-2-controlled autophagy reveals spermidine, MK-2206, and niclosamide as putative antiviral therapeutics (Microbiology).

Hadjadj, J., Yatim, N., Barnabei, L., Corneau, A., Boussier, J., Smith, N., Péré, H., Charbit, B., Bondet, V., Chenevier-Gobeaux, C., et al. (2020). Impaired type I interferon activity and inflammatory responses in severe COVID-19 patients. Science eabc6027.

Haviernik, J., Štefánik, M., Fojtíková, M., Kali, S., Tordo, N., Rudolf, I., Hubálek, Z., Eyer, L., and Ruzek, D. (2018). Arbidol (Umifenovir): A Broad-Spectrum Antiviral Drug That Inhibits Medically Important Arthropod-Borne Flaviviruses. Viruses 10, 184.

Hoffmann, M., Kleine-Weber, H., Krueger, N., Mueller, M. A., Drosten, C., and Poehlmann, S. (2020). The novel coronavirus 2019 (2019-nCoV) uses the SARS-coronavirus receptor ACE2 and the cellular protease TMPRSS2 for entry into target cells (Molecular Biology).

Jeon, S., Ko, M., Lee, J., Choi, I., Byun, S. Y., Park, S., Shum, D., and Kim, S. (2020). Identification of antiviral drug candidates against SARS-CoV-2 from FDA-approved drugs (Microbiology).

Li (2020). An exploratory randomized controlled study on the efficacy and safety of lopinavir/ritonavir or arbidol treating adult patients hospitalized with mild/moderate COVID-19 (ELACOI). MedRxiv 33.

Lu, Y., Liu, D. X., and Tam, J. P. (2008). Lipid rafts are involved in SARS-CoV entry into Vero E6 cells. Biochem. Biophys. Res. Commun. 369, 344-349.

Maisonnasse, P., Guedj, J., Contreras, V., Behillil, S., Solas, C., Marlin, R., Naninck, T., Pizzorno, A., Lemaitre, J., Gonsalves, A., et al. (2020). Hydroxychloroquine use against SARS-CoV-2 infection in non-human primates. Nature.

Richardson, P., Griffin, I., Tucker, C., Smith, D., Oechsle, O., Phelan, A., and Stebbing, J. (2020). Baricitinib as potential treatment for 2019-nCoV acute respiratory disease. The Lancet 395, e30-e31.

Riva, L., Yuan, S., Yin, X., Martin-Sancho, L., Matsunaga, N., Pache, L., Burgstaller-Muehlbacher, S., De Jesus, P. D., Teriete, P., Hull, M. V., et al. (2020). Discovery of SARS-CoV-2 antiviral drugs through large-scale compound repurposing. Nature.

Schneider, M., Ackermann, K., Stuart, M., Wex, C., Protzer, U., Schätzl, H. M., and Gilch, S. (2012). Severe Acute Respiratory Syndrome Coronavirus Replication Is Severely Impaired by MG132 due to Proteasome-Independent Inhibition of M-Calpain. J. Virol. 86, 10112-10122.

Stebbing, J., Phelan, A., Griffin, I., Tucker, C., Oechsle, O., Smith, D., and Richardson, P. (2020). COVID-19: combining antiviral and anti-inflammatory treatments. Lancet Infect. Dis. 20, 400-402.

Tu, Y.-F., Chien, C.-S., Yarmishyn, A. A., Lin, Y.-Y., Luo, Y.-H., Lin, Y.-T., Lai, W.-Y., Yang, D.-M., Chou, S.-J., Yang, Y.-P., et al. (2020). A Review of SARS-CoV-2 and the Ongoing Clinical Trials. Int. J. Mol. Sci. 21, 2657.

Wang, Y., Zhang, D., Du, G., Du, R., Zhao, J., Jin, Y., Fu, S., Gao, L., Cheng, Z., Lu, Q., et al. (2020). Remdesivir in adults with severe COVID-19: a randomised, double-blind, placebo-controlled, multicentre trial. The Lancet 50140673620310229.

Williamson, B., Feldmann, F., Schwarz, B., Meade-White, K., Porter, D., Schulz, J., van Doremalen, N., Leighton, I., Yinda, C. K., Perez-Perez, L., et al. (2020). Clinical benefit of remdesivir in rhesus macaques infected with SARS-CoV-2 (Microbiology).

Wu, C., Liu, Y., Yang, Y., Zhang, P., Zhong, W., Wang, Y., Wang, Q., Xu, Y., Li, M., Li, X., et al. (2020). Analysis of therapeutic targets for SARS-CoV-2 and discovery of potential drugs by computational methods. Acta Pharm. Sin. B 10, 766-788.

Zhou, Y., and Simmons, G. (2012). Development of novel entry inhibitors targeting emerging viruses. Expert Rev. Anti Infect. Ther. 10, 1129-1138.

The invention claimed is:

1. A method of treating coronavirus (CoV) infection comprising administering to a patient in need thereof PLD or a pharmaceutically acceptable salt or stereoisomer thereof, wherein PLD or a pharmaceutically acceptable salt or stereoisomer thereof is used in combination with remdesivir.

2. The method according to claim 1, wherein PLD or a pharmaceutically acceptable salt or stereoisomer thereof and remdesivir are administered concurrently, sequentially or separately.

3. The method according to claim 1, wherein the molar ratio of PLD or a pharmaceutically acceptable salt or stereoisomer thereof and remdesivir is from 1:1000 to 1000:1, 1:700 to 700:1, 1:500 to 500:1, 1:300 to 300:1, 1:100 to 100:1, or 1:50 to 50:1.

4. The method according to claim 1, wherein, in addition to PLD or a pharmaceutically acceptable salt or stereoisomer thereof and remdesivir, dexamethasone is also administered.

5. The method according to claim 4, wherein the dexamethasone is administered concurrently, sequentially or separately to PLD or a pharmaceutically acceptable salt or stereoisomer thereof and remdesivir.

6. The method according to claim 1, wherein the patient additionally receives the following medications prior to starting treatment with PLD or a pharmaceutically acceptable salt or stereoisomer thereof:

Ondansetron 8 mg IV (or equivalent);

Diphenhydramine hydrochloride 25 mg IV (or equivalent); and

Ranitidine 50 mg IV (or equivalent).

7. The method according to claim 1, wherein the treatment reduces a risk of coronavirus (CoV) infection.

8. The method according to claim 1, wherein the CoV is SARS-COV-2.

9. The method according to claim 1, wherein the CoV infection is a COVID-19 infection and/or wherein the treatment of the CoV infection comprises treating pneumonia caused by COVID-19.

10. The method according to claim 1, wherein the CoV infection is mild infection.

11. The method according to claim 1, wherein the CoV infection is acute CoV infection.

12. The method according to claim 11, wherein the CoV infection is post-COVID syndrome, COVID persistent or long COVID and wherein the post-CoV syndrome, CoV persistent or long CoV includes one or more symptoms arising from the cardiovascular, respiratory, gastrointestinal, neurological, musculoskeletal, metabolic, renal, dermatological, otolaryngological, haematological and autonomic systems; psychiatric problems, generalised pain, fatigue and/or persisting fever.

13. The method according to claim 1, wherein the treatment comprises treating a patient with signs and symptoms of CoV infection for up to 4 weeks.

14. The method according to claim 1, wherein the treatment comprises reducing risk of or treating COVID persistent, long COVID or post-COVID syndrome.

15. The method according to claim 1, wherein the treatment reduces the infectivity of CoV patients.

16. The method according to claim 1, further comprising administering one or more additional CoV antiviral agent(s), wherein the additional CoV antiviral agent may be selected from MDL28170, E64d and CA-074.

17. A combination of PLD or a pharmaceutically acceptable salt or stereoisomer thereof, and remdesivir.

18. A kit comprising a combination of PLD or a pharmaceutically acceptable salt or stereoisomer thereof, and remdesivir; said kit optionally further comprising instructions for the use of combination(s) according to the present invention for use in the treatment of coronavirus (CoV) infection.

19. A method of reducing viral load in a cell or reducing the infection efficiency of a virus in a cell or reducing viral propagation in a cell or reducing viral replication in a cell, said method comprising contacting a cell with PLD or a pharmaceutically acceptable salt or stereoisomer thereof in combination with remdesivir.

20. The method according to claim 13, wherein the CoV infection is COVID-19.

21. The method according to claim 1, wherein the CoV infection is moderate infection.

22. The method according to claim 1, wherein the CoV infection is severe infection.

23. The method according to claim 1, wherein the CoV infection is ongoing symptomatic CoV infection.

24. The method according to claim 1, wherein the CoV infection is post-COVID syndrome, COVID persistent or long COVID.

25. The method according to claim 1, wherein the treatment comprises treating a patient with signs and symptoms of CoV infection from 4 weeks to 12 weeks.

26. The method according to claim 1, wherein the treatment comprises treating a patient with signs and symptoms of CoV infection for more than 12 weeks.

* * * * *